United States Patent
Pilgaonkar et al.

(10) Patent No.: US 10,391,060 B2
(45) Date of Patent: Aug. 27, 2019

(54) PARTICULATE DELIVERY SYSTEMS

(71) Applicant: RUBICON RESEARCH PRIVATE LIMITED, Mumbai (IN)

(72) Inventors: Pratibha Pilgaonkar, Mumbai (IN); Anilkumar Gandhi, Mumbai (IN); Paras Jain, Mumbai (IN)

(73) Assignee: RUBICON RESEARCH PRIVATE LIMITED, Mumbai (IN)

( * ) Notice: Subject to any disclaimer, the term of this patent is extended or adjusted under 35 U.S.C. 154(b) by 0 days.

(21) Appl. No.: 15/750,722

(22) PCT Filed: Aug. 5, 2016

(86) PCT No.: PCT/IN2016/050261
§ 371 (c)(1),
(2) Date: Feb. 6, 2018

(87) PCT Pub. No.: WO2017/021983
PCT Pub. Date: Feb. 9, 2017

(65) Prior Publication Data
US 2019/0000763 A1    Jan. 3, 2019

(30) Foreign Application Priority Data
Aug. 6, 2015   (IN) .................. 2969/MUM/2015

(51) Int. Cl.
| | | |
|---|---|---|
| *A61K 9/06* | (2006.01) | |
| *A61K 9/14* | (2006.01) | |
| *A61K 9/48* | (2006.01) | |
| *A61K 9/50* | (2006.01) | |
| *A61K 9/51* | (2006.01) | |
| *A61K 45/06* | (2006.01) | |
| *A61K 31/138* | (2006.01) | |
| *A61K 31/506* | (2006.01) | |
| *A61K 31/519* | (2006.01) | |
| *A61K 31/7056* | (2006.01) | |

(52) U.S. Cl.
CPC ............... *A61K 9/148* (2013.01); *A61K 9/06* (2013.01); *A61K 9/4808* (2013.01); *A61K 9/4891* (2013.01); *A61K 9/5015* (2013.01); *A61K 9/5031* (2013.01); *A61K 9/5036* (2013.01); *A61K 9/5123* (2013.01); *A61K 9/5146* (2013.01); *A61K 9/5161* (2013.01); *A61K 31/138* (2013.01); *A61K 31/506* (2013.01); *A61K 31/519* (2013.01); *A61K 31/7056* (2013.01); *A61K 45/06* (2013.01)

(58) Field of Classification Search
None
See application file for complete search history.

(56) References Cited

U.S. PATENT DOCUMENTS 5,997,877 A    12/1999   Chang
7,141,254 B2   11/2006   Bhaskaran et al.

FOREIGN PATENT DOCUMENTS

WO    WO-2009136219 A1    11/2009

OTHER PUBLICATIONS

Sav et al., Journal of Pharmaceutical Investigation (2013), 43(5), pp. 363-373.*
International Search Report issued in PCT/IN2016/050261 dated Dec. 26, 2016.

* cited by examiner

*Primary Examiner* — Brian J Davis
(74) *Attorney, Agent, or Firm* — Blank Rome LLP

(57) ABSTRACT

The present invention provides particulate delivery systems comprising plurality of particles comprising fenugreek gum and at least one pharmaceutically acceptable excipient. The particulate delivery systems of the present invention are used for the delivery of therapeutic, immunologic or diagnostic agents, and the like.

21 Claims, No Drawings

PARTICULATE DELIVERY SYSTEMS

This application is the U.S. national phase of International Patent Application No. PCT/IN2016/050261, filed Aug. 5, 2016, which claims the benefit of Indian Patent Application No. 2969/MUM/2015, filed Aug. 6, 2015.

FIELD OF THE INVENTION

The present invention relates to particulate delivery systems comprising fenugreek gum. Particularly, the present invention provides particulate delivery systems comprising plurality of particles comprising fenugreek gum and at least one pharmaceutically acceptable excipient. The particulate delivery systems of the present invention are used for the delivery of therapeutic, immunologic or diagnostic agents, and the like.

BACKGROUND OF THE INVENTION

There has been a considerable research interest in the area of particulate delivery systems as carriers for small and large molecules. The concept of using particles to deliver therapeutic agents has gained tremendous interest over years. Particulate delivery systems can change the fate of a drug without modifying the chemical structure, and increase efficacy and decrease toxicity of a drug. Some particulate drug delivery systems having better capability to overcome physiological barriers, precisely control the release rates, or target drugs to a specific body site, have a marked impact on the health care system.

Particulate systems especially nano- and micro scale based systems offer versatility by virtue of their small size and efficient carrier characteristics, enabling the tailoring of delivery systems with consideration of the biological target, desired pharmacokinetic profile, and route of administration. Both nano scale (1-100 nm) and micro scale (0.1-1000 µm) systems have been extremely important in developing various clinically useful particulate delivery systems. Nanotechnology has been strategically used for developing such particulate delivery systems.

Nanocarriers and microcarriers such as nanoparticles, nanospheres, nanoemulsions, nanocapsules, liposomes, micelles, microparticles, microspheres, and the like demonstrate a broad variety of useful properties, such as controlled or modified drug release; uptake through biological membranes, longevity in the blood allowing for their accumulation in pathological areas with compromised vasculature; specific targeting to certain disease sites due to various targeting ligands attached to the surface of the carriers; enhanced intracellular penetration with the help of surface-attached cell-penetrating molecules; contrast properties due to the carrier loading with various contrast materials allowing for direct carrier visualization in vivo; stimuli-sensitivity allowing for drug release from the carriers under certain physiological conditions, and others.

Such nano- and micro scale based particulate delivery systems comprising multitude of particulate units also provide many advantages over single-unit systems or systems having larger particle size, like reduced risk of local irritation and toxicity, predictable bioavailability, reduced likelihood of dose dumping, minimized fluctuations in the plasma concentration of the biological agent, high dose-strength administration, reduced risk of systemic toxicity and site specific or targeted therapeutic effect, controllable particle size, flexibility of delivering by various routes of administration, more reproducible pharmacokinetic behavior, lower intra- and inter-subject variability than conventional single unit formulations.

Many attempts have been made towards the preparation of particulate delivery systems employing different nanotechnology processes and different particulate carrier materials. U.S. Pat. No. 5,766,635 discloses preparation of nanoparticles by dissolving a poly (ethylene oxide) and/or poly (propylene oxide) polylactic copolymer in an organic solvent followed by mixing the solution containing the polymer with an aqueous solution and by precipitation or by microfluidization and solvent evaporation. U.S. Pat. No. 8,293,276 discloses methods of making nanoparticles having about 0.2 to about 35 weight percent of a therapeutic agent; and about 10 to about 99 weight percent of a polymer such as a diblock poly (lactic) acid-poly (ethylene) glycol. Schubert et al. describe in Journal of Polymer Science, Part A, Polymer Chemistry, Vol. 48, 3924-3931, 2010, the preparation of nanoparticles from solutions of poly (methyl methacrylate) and its copolymers by nanoprecipitation method. US Patent Application 20100297237 discloses a pharmaceutical composition comprising nanoparticles comprising: a poorly water soluble drug; a poorly aqueous soluble non-ionizable polymer selected from the group consisting of ethylcellulose, cellulose acetate, cellulose propionate, cellulose butyrate, cellulose acetate butyrate, and mixtures thereof; and an amine-functionalized methacrylate copolymer, poly [ethylacrylate-co-methyl methacrylate-co-trimethylamonioethyl methacrylate chloride].

Though various attempts have been made to develop particulate delivery systems using synthetic polymers, these polymers may be toxic, non-biodegradable, allergic, incompatible with some drugs, or not economical. Natural excipients are therefore employed in particulate delivery systems as they are inert, safe, non-toxic, biocompatible, biodegradable, economical, eco-friendly and abundantly available in nature compared to the synthetic polymers. Natural polysaccharides have been widely investigated for their benefits in particulate delivery systems.

Polysaccharides consist of long carbohydrate molecules containing repeated monosaccharide units which are joined together by means of glycosidic bonds. They represent the most abundant biomolecules in nature. Polysaccharides are highly biocompatible and biodegradable. They can be classified by their origin: vegetal origin (e.g. pectin), algal origin (e.g. alginate), microbial origin (e.g. dextran, xanthan gum), and animal origin (chitosan, heparin). Polysaccharides may also be classified by their charge: cationic (chitosan), anionic (hyaluronic acid, heparin) and nonionic (dextran). Polysaccharides can be homopolysaccharides or heteropolysaccharides depending on their monosaccharide components. A variety of particulate delivery systems have been attempted using different polysaccharides.

U.S. Pat. No. 6,677,386 discloses a process for producing starch nanoparticles in which the starch is plasticized using shear forces and a crosslinking agent is added during the processing. After the processing, starch was dissolved or dispersed in an aqueous medium to a concentration between 4 and 40 wt. % which results in starch nanoparticles that are characterized by an average particle size of less than 400 nm. Preparation of nanoparticles using other natural polysaccharides has also been discussed. U.S. Pat. No. 8,389,012 discusses nanoparticulate controlled-release composition containing gellan gum and polyethylene glycol and their methods of preparation. PCT Publication WO2007/042572 provides nanoparticulate systems comprising chitosan, and optionally a polyoxyethynylenated derivative which are ionically crosslinked for the controlled release of heparin. Senthil et al describe in World Journal of Pharmacy and Pharmaceutical Sciences, Volume 3, Issue 9, 978-1015, 2014, the development and evaluation of enteric coated guar gum nanoparticles of antiprotozoal fixed drugs combination of Tinidazole and Norfloxacin for treatment of amoebiasis. Guar gum nanoparticles were prepared by double step w/o/w emulsion method, cross linking with glutaraldehyde and enteric coated by solvent evaporation method to protect the drugs in gastric fluids and achieve a targeted drug delivery.

The majority of natural polysaccharides present several hydrophilic groups such as carboxyl, hydroxyl and amino groups, which endow their solubility in water and the formation of non-covalent bonds with biological tissues and mucosal membranes. This way, the hydrophilic properties of most of the polysaccharide nanoparticles provide bioadhesion and mucoadhesion characteristics to these biomaterials, as well as the possibility of chemical modification of the macromolecules to bind drugs or targeting agents. The hydrophilic nanoparticles also possess the enormous advantage of extended circulation in blood, which increases the probability of passive targeting of the nanoparticles into the tumor tissues. Though a number of benefits are associated with the use of natural polysaccharides in particulate delivery systems, certain drawbacks such as batch to batch variation, low drug release predictability as well as other disadvantages otherwise associated with particulate delivery systems such as erratic release profile, low drug loading capacity, particle-particle aggregation may however exist. A need therefore exists to identify and evaluate newer natural biomaterials as carrier materials for particulate delivery systems that can overcome one or more of the drawbacks of natural excipient based particulate systems.

The present inventors after rigorous experimentation have identified unexpected benefits associated with the use of fenugreek gum as a carrier material in particulate delivery systems. The present inventors provide particulate delivery systems comprising plurality of particles comprising fenugreek gum and at least one pharmaceutically acceptable excipient. The systems of the present invention overcome one or more of the drawbacks associated with particulate delivery systems and/or use of natural polysaccharides therein as mentioned hereinabove. Fenugreek gum has not been reported previously by researchers to be useful as a carrier material for preparation of plurality of particles for particulate delivery systems. Fenugreek gum employed in the particulate delivery systems of the present invention serves as a non-toxic, ecofriendly, economical biodegradable alternative to existing natural polysaccharides and is amenable to nanotechnological processes for the development of particulate delivery systems of a variety of therapeutic, immunologic, or diagnostic agents, for controlled delivery, targeting to specific biological tissues, improved stability and the like.

SUMMARY OF THE INVENTION

The present invention provides particulate delivery systems comprising plurality of particles comprising fenugreek gum and at least one pharmaceutically acceptable excipient. The particulate delivery systems of the present invention are used for the delivery of therapeutic, immunologic or diagnostic agents, and the like.

DETAILED DESCRIPTION OF THE INVENTION

The present invention relates to particulate delivery systems comprising fenugreek gum. Particularly, the present invention provides particulate delivery systems comprising plurality of particles comprising fenugreek gum and at least one pharmaceutically acceptable excipient. In a further embodiment, the particulate delivery systems of the present invention comprise plurality of particles comprising fenugreek gum, at least one pharmaceutically acceptable excipient and optionally at least one active agent. In another embodiment, the particulate delivery systems of the present invention comprise plurality of particles comprising at least one active agent, fenugreek gum, and at least one pharmaceutically acceptable excipient.

The term "particulate delivery systems" employed herein refers to systems for delivery to the subject in need thereof plurality of particles of nanoscale and microscale size comprising fenugreek gum, at least one pharmaceutically acceptable excipient and optionally at least one active agent. Further, the term "particles of nanoscale size" as used herein refers to particles of size of up to about 100 nanometers (nm). In another embodiment, the particles of the nanoscale size have a size of about 0.1 nm to about 100 nm. The term "particles of microscale size" as used herein refers to particles of size of up to about 1000 micrometers (μm). In a further embodiment, the particles of microscale size have a size of about 0.1 μm to about 1000 μm. In another embodiment, the particles of microscale size have a size of about 0.1 μm to about 500 μm. The term "particles of nanoscale and microscale size" as used herein refers to particles of size of up to about 1000 μm. In another embodiment, the particles of nanoscale and microscale size have a size of about 0.1 nm to about 1000 μm. In a further embodiment, the particles of nanoscale and microscale size have a size of about 0.5 nm to about 500 μm.

Furthermore, the term "particles" employed herein refers to the carrier particles incorporated in the delivery systems of the present invention and may be, but are not limited to, nanoparticles, nanospheres, nanocapsules, microparticles, microspheres, microcapsules, liposomes, nanoemulsions, solid lipid nanoparticles, and the like or mixtures thereof. In another embodiment, carrier particles incorporated in the delivery system of the present invention may be, but are not limited to, nanoparticles, nanospheres, microparticles, or microspheres.

The terms "delivery system", "formulation" or "composition" have been used interchangeably for the purpose of the present invention.

The particulate delivery systems of the present invention comprise plurality of particles comprising fenugreek gum. Fenugreek gum incorporated in the particulate delivery system of the present invention comprises not less than about 15% by weight of galactomannan. In a further embodiment, the fenugreek gum employed in the delivery system of the present invention comprises from about 15% to about 100% by weight of galactomannan. In yet another embodiment, the fenugreek gum incorporated in the delivery system of the present invention comprises not less than about 25% by weight of galactomannan. In another embodiment, the fenugreek gum incorporated in the delivery system of the present invention comprises not less than about 50% by weight of galactomannan. In yet another embodiment, the fenugreek gum incorporated in the delivery system of the present invention comprises not less than about 60% by weight of galactomannan. In a further embodiment, the fenugreek gum incorporated in the delivery system of the present invention comprises about 70% by weight of galactomannan. In another embodiment, the fenugreek gum incorporated in the delivery system of the present invention comprises about 80% by weight of galactomannan. In one embodiment, the fenugreek gum incorporated in the delivery system of the present invention comprises about 85% by weight of galactomannan. In another embodiment, the fenugreek gum employed in the delivery system of the present invention comprises from about 50% to about 95% by weight of galactomannan. In a further embodiment, the fenugreek gum employed in the delivery system of the present invention comprises from about 50% to about 98% by weight of galactomannan.

Fenugreek galactomannan consists of β-1-4-linked linear mannan backbone, to which galactose grafts are linked randomly by α, 1-6 glycoside bond. Galactose grafts are linked nearly on all the mannose groups on the mannan backbone. The ratio of galactose to mannose in fenugreek galactomannan is therefore approximately 1:1. Galactomannan is predominantly present in fenugreek seeds of fenugreek plant (*Trigonella foenum-graecum*) and is the soluble fiber component thereof.

In another embodiment, the fenugreek gum may comprise in addition to galactomannan, insoluble fibers including, but not limited to, cellulose, hemicellulose, lignin, and the like; proteins; tannins, alkaloids, or amino acids and the like. In one embodiment, the fenugreek gum employed in the delivery systems of the present invention comprises not more than about 85% by weight of insoluble fibers. In another embodiment, the fenugreek gum employed in the delivery systems of the present invention comprises not more than about 80% by weight of insoluble fibers. In a further embodiment, the fenugreek gum employed in the delivery system of the present invention comprises not more than about 50% by weight of insoluble fibers. In another embodiment, the fenugreek gum employed in the delivery system of the present invention does not comprise any insoluble dietary fibers. In a further embodiment, the fenugreek gum employed in the delivery systems of the present invention may comprise not more than about 10% by weight of proteins. In another embodiment, the fenugreek gum employed in the delivery systems of the present invention may comprise not more than about 5% by weight of proteins. In another embodiment, the fenugreek gum employed in the compositions of the present invention may comprise not more than about 5% by weight of alkaloids. In another embodiment, fenugreek gum employed in the compositions of the present invention may comprise not more than about 1% by weight of alkaloids. In one embodiment, fenugreek gum employed in the compositions of the present invention may comprise not more than about 0.1% by weight of alkaloids. In a further embodiment, alkaloids above detectable limits may not be present in the compositions of the present invention. In a further embodiment, alkaloids may be absent in the fenugreek gum employed in the compositions of the present invention. In another embodiment, tannins may be absent in the fenugreek gum employed in the compositions of the present invention. In yet another embodiment, amino acids may be absent in the fenugreek gum employed in the compositions of the present invention. In a further embodiment, fenugreek gum employed in the particulate delivery system of the present invention comprises not less than about 15% by weight of galactomannan, not more than about 80% by weight of insoluble fibers and not more than about 5% by weight of proteins. In another embodiment, fenugreek gum employed in the particulate delivery system of the present invention comprises not less than about 15% by weight of galactomannan, not more than about 80% by weight of insoluble fibers, not more than about 5% by weight of proteins and alkaloids, tannins and amino acids below detection limits. In a further embodiment, fenugreek gum employed in the compositions of the present invention has a viscosity of not less than about 10000 cps at 2% w/v concentration at 25° C.

In one embodiment, fenugreek gum may be obtained from fenugreek seeds of fenugreek plant (*Trigonella foenum-graecum*). In a further embodiment, fenugreek gum may be obtained from testa and endosperm part of the fenugreek seeds. In another embodiment, fenugreek gum comprising galactomannan employed in the particulate delivery system of the present invention may be obtained from fenugreek seeds by different non-limiting methods as disclosed in US Patent Application 20050084549, or US Patent Application 20130041043, and incorporated herein by reference. In a further embodiment, fenugreek gum may be obtained from fenugreek seeds by any method known in the art.

In a further embodiment, fenugreek gum employed in the delivery systems of the present invention may be modified. In another embodiment, fenugreek gum employed in the delivery systems of the present invention may be chemically modified. In yet another embodiment, fenugreek gum employed in the delivery systems of the present invention may be physically modified. In a further embodiment, fenugreek gum may be ionically modified. In another embodiment, fenugreek gum employed in the compositions of the present invention may be chemically modified by modifications such as, but not limited to, carboxymethylation, oxidation, esterification, alkylation, methylation, acetylation, hydroxypropylation, benzoylation, hydroxylation, sulfonation, graft copolymerization or the like or any combinations thereof. In a further embodiment, fenugreek gum employed in the compositions of the present invention may be physically modified by methods, such as, but not limited to, heating, high pressure treatment, microwaving, and the like or any combinations thereof. In a further embodiment, the fenugreek gum of the present invention may be modified chemically, physically, ionically or by combinations thereof. In a further embodiment, the fenugreek gum may be modified chemically, physically, ionically or by combinations thereof to modify various properties thereof, such as, but not limited to, solubility, viscosity, swelling capacity, flow property, gel strength, dissolution rate, disintegration rate, water holding capacity, ionic binding or complexation properties, and the like or combinations thereof. In a further embodiment, fenugreek gum may be ionically modified to make it cationic, anionic or amphoteric. In another embodiment, functionalized fenugreek gum may be employed. In one embodiment, functionalized fenugreek gum may be, but is not limited to, -carboxy functionalized fenugreek gum, -amine functionalized fenugreek gum, and the like or combinations thereof. In still another embodiment, fenugreek gum is functionalized by chemical modification as discussed herein above. In one embodiment, fenugreek gum may be modified to make it hydrophobic in nature. In another embodiment, fenugreek gum may be modified to make it amphiphilic in nature.

In one embodiment, the carrier particles and particulate delivery systems of the present invention may comprise about 0.1% to about 99% by weight of fenugreek gum. In a further embodiment, the carrier particles and particulate delivery systems of the present invention may comprise about 0.5% to about 99% by weight of fenugreek gum. In another embodiment, the carrier particles and particulate delivery systems of the present invention may comprise about 0.5% to about 95% by weight of fenugreek gum. In a further embodiment, the amount of fenugreek gum incorporated in the particulate delivery systems of the present invention is based on the type of carrier particle being prepared and the final dosage form for the delivery of the plurality of particles. In one embodiment, the carrier particles comprise at least 15% by weight of fenugreek gum. In another embodiment, the carrier particles comprise about 15% to about 99% by weight of fenugreek gum. In a further embodiment, the carrier particles comprise about 25% to about 95% by weight of fenugreek gum. In another embodiment, the carrier particles comprise about 35% to about 85% by weight of fenugreek gum.

Without being bound to any theory it is believed that fenugreek gum employed in the particulate delivery system of the present invention is useful as a carrier material for the preparation of the particulate delivery systems since fenugreek galactomannan has very few (~1%) unsubstituted mannoses in the mannan backbone and therefore no large unsubstituted (or nonhairy) regions on the backbone, resulting in lower or practically no chain-chain interactions between molecules of fenugreek galactomannan. This is advantageous for the particulate delivery systems as the particle-particle or chain-chain interactions generally causing aggregations during the preparation of and after the formation of carrier particles and the particulate delivery systems is unexpectedly controlled with the use of fenugreek galactomannan. It is further believed, that unlike other polymers, though hydrogen bonding interactions amongst galactose units of adjacent chains of galactomannan are favored in fenugreek gum, the absence of non-hairy blocks on fenugreek mannan backbone and the presence of C-2, C-3 hydroxyl pair in mannose and the C-3, C-4 hydroxyl pair in galactose in cis-configuration resulting in freedom of rotation around 1→6 glycosidic linkage, prevents any zipping type hydrogen bonding interaction between mannose molecules of adjacent polymer chains, thereby preventing hyperentanglement and any close solid state packing of polymer chains during preparation of carrier particles or agglomeration of formed particles while providing colloidal dispersions of fenugreek gum in aqueous media having good physical stability. The unexpected lack of agglomeration during preparation of carrier particles and in the final product with the use of fenugreek gum is believed to reduce cumbersome, expensive, and time-consuming processing steps that may otherwise be required for preparation of carrier particles using other polymers that create aggregation issues. Furthermore, the C-2, C-3 hydroxyl pair in mannose and the C-3, C-4 hydroxyl pair in galactose have cis-configuration, making rotation possible around an interpyranose glycoside bond in the fenugreek galactomannan. The presence of cis-hydroxyl pair along with an essentially linear chain configuration provides fenugreek galactomannan flexibility for the preparation of particulate delivery systems that generally require carrier materials that are amenable to use under various nanotechnological processes and or delivery of variety of actives by various routes of administration. It is also believed that the complete galactose grafted hydrophobic mannan backbone of fenugreek gum having hydrophilic exterior galactose layer, serves to reduce interfacial or surface tension, imparting increased surface stability or emulsion stability to the particulate carriers or delivery systems or during preparation thereof depending on the preparation methods and type of particulate carriers being prepared. It is believed that the fenugreek gum forms the matrix of the carrier particles or is a matrix forming agent for the carrier particles of the present invention. It is further believed without being bound to any theory that fenugreek gum forms hydrogel matrix.

In one embodiment, fenugreek gum employed in the delivery systems of the present invention provides stable nanoscale or microscale particulate formulations. In another embodiment, fenugreek gum employed in the delivery systems of the present invention provides non-aggregating nanoscale or microscale particulate formulations. In one embodiment, fenugreek gum employed in the delivery systems of the present invention provides substantially non-aggregating nanoscale or microscale particulate formulations.

In a further embodiment, the carrier particles incorporated in the particulate delivery systems of the present invention have D90 in the range of about 10 nm to about 1000 μm. In another embodiment, the carrier particles incorporated in the particulate delivery systems of the present invention have D90 in the range of about 25 nm to about 1000 μm. In yet another embodiment, the carrier particles incorporated in the particulate delivery systems of the present invention have D90 in the range of about 50 nm to about 1000 μm. The term D90 as used herein refers to the size value corresponding to cumulative size distribution at 90%, which represents the size of particles below which 90% of the sample lies. In another embodiment, polydispersity index of the carrier particles of the present invention is not more than 5. In a further embodiment, polydispersity index of the carrier particles of the present invention is not more than 3. In a further embodiment, polydispersity index of the carrier particles of the present invention is not more than 2. In one embodiment, the polydispersity index of the carrier particles of the present invention is not more than 1. In another embodiment, the polydispersity index of the carrier particles of the present invention is not more than 0.5. The term polydispersity index, as used herein, is a measure for the size distribution of the carrier particles of the present invention with an increasing number describing a broadening size distribution.

The plurality of particles in the particulate delivery system of the present invention comprising fenugreek gum further comprise at least one pharmaceutically acceptable excipient. In one embodiment, the at least one pharmaceutically acceptable excipient is employed in the preparation of the carrier particles of the particulate delivery system of the present invention. The at least one pharmaceutically acceptable excipient that may be employed along with fenugreek gum in the preparation of plurality of particles of the delivery system of the present invention include, but are not limited to, surfactants, synthetic polymers, natural polymers, surface modifiers, crosslinking agents, solvents, complexing agents, lipids, pH modifiers and the like or mixtures thereof.

Suitable surfactants that may be employed in the delivery systems of the present invention include, but are not limited to, anionic, cationic, non-ionic or zwitterionic/amphoteric surfactants. In a further embodiment, surfactants of varying HLB values from about 1 to about 20 may be employed in the delivery systems of the present invention. Non-limiting examples of anionic surfactants that may be employed are sodium stearate, sodium dodecyl sulfate, sodium dodecyl benzene sulfonate, sodium lauryl sulfate, dioctyl sodium sulfosuccinate, sodium dehydrocholate, sodium taurocholate, sodium glycocholate, sodium cholate, sodium oleate, sodium caprylate, polyether sulfonate (e.g. Tritons X-200K®, an alkyl aryl polyether sulfonate), stearic acid, calcium stearate, and the like or combinations thereof. Non-limiting examples of cationic surfactants that may be employed are laurylamine hydrochloride, trimethyl dodecylammonium chloride, cetyl trimethylammonium bromide, cetrimonium bromide, chlorhexidine salts, dodecyltrimethylammonium bromide, 1,2-dioleoyl-3-trimethylammonium-propane, dimethyldiocta-decylammonium bromide, polyoxyethylene alcohol, alkylphenol ethoxylate, polyoxyethylene sorbitan fatty esters (e.g. polysorbate 80, polysorbate 20, polysorbate 60, polysorbate 85), propylene oxide-modified polymethylsiloxane, benzalkonium chloride, triethanolamine, and the like or combinations thereof. Non-limiting examples of non-ionic surfactants that may be employed are mono- and diglycerides, medium chain glyceride (Capmul), glyceryl monooleate (Peceol), glyceryl ricinoleate, glyceryl laurate, glyceryl caprylate (Capmul MCM), PEG sorbitan fatty acid esters like PEG-20 sorbitan monolaurate (Tween 20), PEG 20 sorbitan monostearate (Tween 60), PEG sorbitan monooleate (Tween 80), sorbitan fatty acid esters like sorbitan monolaurate (Span 20), sorbitan monooleate (Span 80) caprylocaproyl polyoxylglycerides (e.g. Labrasol), sugar ester or sucrose ester surfactants such as, but not limited to, sucrose distearate (sucro ester 7), olyoxyethylene(20)cetyl ether, polyoxyethylene(20) isohecadecyl ether, tyloxapol, polyoxyethylene(20) oleyl ether, polyoxyethylene(20) stearyl ether, poloxamers (e.g., Pluronics F68® and F108®, which are block copolymers of ethylene oxide and propylene oxide, Poloxamer 407), poloxamines (e.g., Tetronic 908® also known as Poloxamine 9085®, Tetronic 1508®, which is a tetrafunctional block copolymer derived from sequential addition of propylene oxide and ethylene oxide to ethylenediamine, Tetronic 904®), mixture of sucrose stearate and sucrose distearate (e.g., Crodestas F-110®), p-isononylphenoxypoly-(glycidol) (also known as Olin-IOG® or Surfactant 10-G®), sucrose cocoate and alcohol (Crodestas SL-40®), d-α-tocopheryl polyethylene glycol 1000 succinate (Vit E TPGS), glycerol monostearate, cetostearyl alcohol, cetomacrogol emulsifying wax, polyoxyethylene alkyl ethers (macrogol ethers such as cetomacrogol 1000), polyoxyethylene castor oil derivatives, polyethylene glycols (e.g., Carbowax 3550® and 934®), polyoxyethylene stearates, and the like or combinations thereof. Non-limiting examples of amphoteric surfactants that may be employed are dodecyl betaine, lauramidopropyl betaine, cocoamido-2-hydroxypropyl sulfobetaine and the like or combinations thereof. In a further embodiment, surfactants may be employed in the delivery systems of the present invention as, but not limited to, emulsifying agent, suspending agent, surface modifier, stabilizer, solubilizer, and the like. In one embodiment, the amount of surfactant that may be employed is about 0.001% to about 25% by weight of the delivery system. In a further embodiment, the amount of surfactant that may be employed is about 0.01% to about 20% by weight of the delivery system.

Synthetic polymers that may be employed in the carrier particles of the particulate delivery system of the present invention include, but are not limited to, cellulose derivatives, vinyl derivatives or polymers or copolymers thereof, polyalkylene oxides and derivatives thereof, maleic copolymers, acrylic acid derivatives, polyesters, poly (acrylamides) polyanhydrides, pegylated polymers, copolymers and derivatives thereof, polyalkyl (cyanoacrylate) polymers, copolymers and derivatives thereof, polystyrene polymers, copolymers, and derivatives thereof, polyamines, copolymers or derivatives thereof, polyphosphazene, polyoxazolines, and the like or combinations thereof. Suitable cellulose derivatives that may be employed include, but are not limited to, ethyl cellulose, methylcellulose, hydroxypropylmethylcellulose (HPMC), hydroxypropyl cellulose (HPC), hydroxy ethyl cellulose, hydroxymethyl cellulose, hydroxypropyl ethylcellulose, carboxymethylethyl cellulose, carboxy ethylcellulose, carboxymethyl hydroxyethylcellulose, hydroxyethylmethyl carboxymethyl cellulose, hydroxyethyl methyl cellulose, carboxymethyl cellulose, methylhydroxyethyl cellulose, methylhydroxypropyl cellulose, carboxymethyl sulfoethyl cellulose, sodium carboxymethyl cellulose, calcium carboxymethyl cellulose, nitrocellulose, non-crystalline cellulose, cellulose acetate, cellulose acetate butyrate, hydroxypropylmethylcellulose acetate succinate, hydroxypropylmethylcellulose phthalate, hydroxymethyl ethylcellulose phthalate, cellulose acetate phthalate, cellulose acetate succinate, cellulose acetate maleate, cellulose acetate trimelliate, cellulose benzoate phthalate, cellulose propionate phthalate, methylcellulose phthalate, ethylhydroxy ethylcellulose phthalate, and the like or combinations thereof. Suitable vinyl derivatives, polymers and copolymers thereof that may be employed include, but are not limited to, polyvinylacetate aqueous dispersion (Kollicoat® SR 30D), copolymers of vinyl pyrrolidone, copolymers of polyvinyl alcohol, mixture of polyvinyl acetate and polyvinylpyrrolidone (e.g. Kollidon® SR), polyvinyl alcohol phthalate, polyvinylacetal phthalate, polyvinyl butylate phthalate, polyvinylacetoacetal phthalate, polyvinylpyrrolidone (PVP), poly (vinylpyridine), polyvinyl chloride, polyvinyl carbonate, polyvinyl alcohol, poly(N-vinyl lactams), polyvinylamines, or combinations thereof. Suitable polyalkylene oxides and derivatives thereof that may be employed include, but are not limited to, polyethylene oxide and the like or any combinations thereof. Suitable acrylic acid derivatives that may be employed include, but are not limited to, methacrylic acids, polymethacrylic acids, polyacrylates, poly alkyl (methacrylate), polymethacrylates, copolymers and derivatives thereof and the like or combinations thereof. Suitable polymethacrylates or poly alkyl methacrylate, copolymers or derivatives thereof that may be employed include, but are not limited to, a) copolymer formed from monomers selected from methacrylic acid, methacrylic acid esters, acrylic acid and acrylic acid esters b) copolymer formed from monomers selected from butyl methacrylate, (2-dimethylaminoethyl) methacrylate and methyl methacrylate c) copolymer formed from monomers selected from ethyl acrylate, methyl methacrylate and trimethylammonioethyl methacrylate chloride or d) copolymers of acrylate and methacrylates with/without quarternary ammonium group in combination with sodium carboxymethylcellulose, e.g. those available from Rohm GmbH under the trademark Eudragit® like Eudragit EPO (dimethylaminoethyl methacrylate copolymer; basic butylated methacrylate copolymer), Eudragit RL and RS (trimethylammonioethyl methacrylate copolymer), Eudragit NE30D and Eudragit NE40D (ethylacrylate methymethacrylate copolymer), Eudragit® L 100 and Eudragit® S (methacrylic acid methyl methacrylate copolymer), Eudragit® L 100-55 (methacrylic acid ethyl acrylate copolymer), Eudragit RD 100 (ammoniomethacrylate copolymer with sodium carboxymethylcellulose); methyl acrylate acrylic acid copolymer, methyl acrylate methacrylic acid copolymer, butyl acrylate styrene acrylic acid copolymer and the like or any combinations thereof. Maleic copolymer based polymers include, but are not limited to, vinylacetate-maleic acid anhydride copolymer, styrenemaleic acid anhydride copolymer, styrenemaleic acid monoester copolymer, vinylmethylether maleic acid anhydride copolymer, ethylene maleic acid anhydride copolymer, vinylbutylether maleic acid anhydride copolymer, acrylonitrilemethyl acrylatemaleic acid anhydride copolymer, butyl acrylate styrenemaleic acid anhydride copolymer and the like, or combinations thereof. Suitable polyesters that may be employed include, but are not limited to, polylactic acid polymers and copolymers thereof such as, but are not limited to, polylactide (PLA), poly-(lactide-co-glycolide) (PLGA); poly-ε- caprolactone; polyglycolic acid polymers and copolymers thereof; polyhydroxy alkanoates; polybutylene succinate; poly (ethylene adipate); and the like or combinations thereof. Suitable pegylated polymers, copolymers and derivatives thereof, include, but are not limited to, PEG-phospholipid, PEG-cholesterol, PEG-cholesterol derivative, PEG-vitamin A, PEG-vitamin E and the like or mixtures thereof. Suitable polystyrene polymers, copolymers, and derivatives thereof, such as but not limited to polystyrene, styrene acrylic acid copolymer, carboxy or amino functionalized polystyrene and the like or combinations thereof may be employed in the delivery systems of the present invention. Suitable polyalkyl (cyanoacrylate) polymers, copolymers and derivatives thereof, such as, but not limited to, poly (isobutylcyanoacrylate), poly (butylcyanoacrylate), polyhexylcyanoacrylate, and the like or combinations thereof may be employed. Natural polymers that may be employed in the present invention include, but not limited to, gelatin; casein; cholesterol; tragacanth; dextran; collagen; alginates; cellulose; albumin; lectins; legumin; vicillin; pullulan; gliadin; agarose; starch and starch-based polymers such as but not limited to, pre-gelatinized starch and the like or mixtures thereof; chitosan; maltodextrin; polysaccharide gums such as, but not limited to, xanthan gum, guar gum, locust bean gum, galactomannans, gellan, konjac, inulin, karaya gum, gum acacia, heparin, hyaluronan, pectin, amino acids, natural polyamines such as but not limited to spermidine, spermine, putrescine, and the like or mixtures thereof; and the like or combinations thereof.

In a further embodiment, one or more natural or synthetic polymer employed in the delivery system of the present invention along with fenugreek gum may be a polycation, a polyanion or a polyamphoteric polymer.

In one embodiment, fenugreek gum employed in the carrier particles of the present invention may be used along with one or more synthetic or natural polymers listed hereinabove for the preparation of carrier particles of the present delivery systems. In a further embodiment, fenugreek gum employed in the carrier particles of the present invention may be modified using one or more synthetic or natural polymers listed herein above. In another embodiment, fenugreek gum may be modified using one or more synthetic or natural polymers listed herein above by various methods, such as but not limited to, graft copolymerization, covalent modification, ionic interactions, complexation, and the like or combinations thereof. In a further embodiment, the fenugreek gum and at least one synthetic or natural polymer may be employed in a proportion of about 1:99 to about 99:1 in the carrier particles of the present invention.

Suitable surface modifiers that may be employed in the delivery systems of the present invention include, but are not limited to, surfactants, synthetic polymers, natural polymers, non-polymeric excipients and the like or combinations thereof. In one embodiment, the surface modifiers stabilize the nanoparticles prepared and may be added during the process of preparation of the nanoparticles or later after formation of nanoparticles. In one embodiment, appropriate surfactants, synthetic polymers or natural polymers as discussed above may be employed as surface modifiers. In a further embodiment, suitable non-polymeric excipients that may be employed in the delivery systems of the present invention as surface modifiers include, but are not limited to, phospholipids, silicas and clays and the like or combinations thereof. Non-limiting examples of phospholipids that may be employed include, but are not limited to, egg phospholipids P123, Lipoid E80, hydrogenated soy phospholipids phospholipon 90H, 100H, 99% pure egg, soy phosphatidyl choline, lysozyme, lecithin (phosphatides), and the like or combinations thereof. Non-limiting examples of silicas and clays that may be employed include, but are not limited to, bentonite, magnesium aluminum silicate (veegum), colloidal silica and the like or mixtures thereof.

In a further embodiment, surface modifiers enlisted hereinabove may be employed to stabilize the carrier particles and/or prevent their aggregation. In a further embodiment, in addition to the above, the surface modifiers may include, but are not limited to, penetration enhancers, targeting ligands, antibodies, agents for preventing reticuloendothelial system uptake, and the like or combinations thereof. Suitable antibodies and targeting ligands as discussed herein below may be attached to the surface of the carrier particles. Non-limiting examples of penetration enhancers include sulfoxides such as, but not limited to, dimethyl sulfoxide, dimethyl formaldehyde, decylmethyl sulphoxide, dimethyl acetamide; atones such as, but not limited to, 1-dodecylazacycloheptan-2-one; pyrrolidones such as, but not limited to, N-methyl-2-pyrrolodones, 2-pyrrolidones; esters such as, but not limited to, propylene glycol monocaprylate, octyl salicylate, oleyl acetate; fatty acids such as, but not limited to, lauric acid, myristic acid, capric acid; oxazolidinones such as, but not limited to, 4-decycloxazolidine-2-one; bile salts and derivatives such as, but not limited to, sodium deoxycholate, sodium taurocholate, sodium taurodihydrofusidate, sodium glycodihydrofusidate, sodium glycocholate, sodium deoxycholate; alkylpyridinium halide; alkyl dimethylbenzyl ammonium halides; essential oils; terpenes and terpinoids such as, but not limited to, cineole, eugenol, d-limonene, linalool, menthol, menthone, basil oil, neem oil, eucalyptus oil; cyclodextrins; vitamin E; phospholipids, amines and amides such as, but not limited to, urea, carbamide, and the like or combinations thereof. Non-limiting examples of agents for preventing reticuloendothelial system uptake include, but are not limited to, hydrophilic surfactants or polymers such as but not limited to, polysorbate 80, poloxamer 188, poloxamer 407, polyethylene glycol, polethyleen oxide, poly-L-lysine and the like or combinations thereof. Suitable complexing agents that may be employed in the preparation of carrier particle include, but are not limited to, phenol, parabens, ascorbic acid, methyl anthranilate, salicylic acid, acetosalicyclic acid, tocopherol, organic acids, carboxylic acids, aromatic acids, aromatic esters, acid salts of amino acids, benzaldehyde, cinnamaldehyde, imidazole, menthol, thiophenol, m-aminobenzoic acid, anthranilic acid, picolinic acids and alkyl esters thereof, toluides, sodium benzoate, methylparaben, sodium methylparaben, para-aminobenzoic acid and esters, sorbic and benzoic acids, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, esters, diethylenetriaminepentaacetic acid (DTPA), 1,4,7,10-tetra-cyclododecane-N,—N',N'',N'''-tetraacetic acid (DOTA), ethylene-diaminetetraacetic acid (EDTA), 1,4,7,10-tetraazacyclododecane-N,N',N''-triacetic acid (D03A), 1,2-diaminocyclohexane-N,N,N',N'-tetraacetic acid (CHTA), ethylene glycol-bis(beta-aminoethylether) N,N,N',N'',-tetraacetic acid (EGTA), 1,4,8,11-tetraazacyclotradecane-N,N', N'',N'''-tetraacetic acid (TETA), and 1,4,7-triazacyclononane-N,N',N'',-triacetic acid (NOT A), cyclodextrin (neutral, charged, native ($\alpha$, $\beta$, $\gamma$, $\delta$, $\epsilon$ cyclodextrin), branched or polymerised or further chemically modified) and the like or mixtures thereof. In one embodiment, the complexing agent if present in the particulate delivery system may be present in an amount from about 0.005% to about 50% by weight of the formulation. In a further embodiment, the complexing agent if present in the particulate delivery system may be present in an amount of about 0.01% to about 45% by weight of the formulation. In another embodiment, the complexing agent if present in the particulate delivery system of the present invention may be present in an amount of about 0.05% to about 40% by weight of the formulation. In a further embodiment, the complexing agent may be employed only during the preparation of the carrier particles. In another embodiment, the complexing agent may be employed during the preparation of carrier particles to remove excess amounts of other excipients, such as but not limited to, surfactants, crosslinking agents and the like that may be employed for the preparation of carrier particles. In one embodiment, complexing agents may be employed as antioxidants during the preparation of carrier particles.

In addition to the other pharmaceutically acceptable excipients that may be incorporated during the preparation of carrier particles of the particulate delivery system of present invention, various solvents such as, but not limited to, organic solvents, inorganic solvents or mixtures thereof may also be employed. In one embodiment, the solvents employed may be water miscible or water immiscible. Non-limiting examples of solvents that may be employed include, but are not limited to, water, acidified water (e.g. water acidified with acids such as, but not limited to phosphoric acid, acetic acid, sulphuric acid, hydrochloric acid, formic acid and the like or combinations thereof), glacial acetic acid solution, acidified methanol, N-methyl pyrrolidone (NMP), dichloromethane, alkaline aqueous solutions, buffers of different pH, pH7.4 phosphate buffer, dimethyl sulfoxide (DMSO), sulfolane, acetone, ethanol, dimethylformamide (DMF), acetophenone, methanol, n-propanol, isopropanol, ethyl acetate, tetrahydrofuran, 1,2-propanediol, 1-n-propyl ether, 1,2-butanediol 1-methyl ether, butyrolactone, cyclohexanone, dimethyl acetamide (DMA), methyl lactate ester, ethyl lactate ester, iso-propyl lactate ester, butyl lactate ester, n-butyl acetate, sec-butyl acetate, isobutyl acetate, propyl acetate, toluene, xylenes, R(+)-limonene, hexane, pentane, heptane, nitrile such as, but not limited to, acetonitrile, cyclic ether such as, but not limited to, dioxane; and the like or mixtures thereof. In a further embodiment, the above solvents may be acidified or basified as needed and employed in the delivery systems of the present invention or during the preparation of carrier particles for the same. In one embodiment, one or more solvents may be employed during the preparation of carrier particles of the particulate delivery systems of the present invention in amounts as necessary depending upon the type of carrier particle being prepared and the method used for the preparation of the carrier particle. In a further embodiment, depending on the final dosage form the particulate delivery system of the present invention may comprise one or more of the solvents listed herein above in suitable amounts.

Suitable cross-linking agents include, but are not limited to, bifunctional aldehydes, diglycolaldehydes, polyaldehydes such as, but not limited to, glutaraldehyde, formaldehyde and the like or combinations thereof; glyoxal, epichlorohydrin, divinyl sulphone, divinyl benzene, genipin, N-hydroxy succinimide, carbodiimide, 1,5-dihalidopentane, 1,9-nonanedithiol, epichlorhydrin, citric acid, succinic acid, malic acid, tartaric acid ethylene glycol dimethacrylate, pentaerythritol tetraacrylate, pentaerythritol triacrylate, 1-[3-(dimethyl amino) propyl]-3-ethylcarbodiimide methiodide, glycerol(bis)acrylate, 3-(acryloyloxy)-2-hydroxypropyl methacrylate, ethylene glycol diacrylate, glycerol, dimethacrylate, divinyl citrate, polycaprolactone (PCL) diacrylate, methyl methacrylate (MMA), divalent or multivalent metal ions (e.g. metal nanoparticles (e.g. gold nanoparticles, silver nanoparticles), functionalized metal nanoparticles), periodate oxidised carbohydrates containing 1,5-dialdehyde moiety, small molecule polycations or polyanions (e.g. triphosphates, sodium tripolyphosphate, sodium hexametaphosphate, sodium borate or borax, salts of calcium, magnesium, barium, ferrous, ferric, copper and the like). In one embodiment, one or more crosslinking agents are employed for covalent crosslinking. In another embodiment, one or more crosslinking agents are employed for ionic crosslinking. In a further embodiment, one or more crosslinking agents may be employed for covalent or ionic crosslinking of fenugreek gum itself. In another embodiment, one or more crosslinking agents may be employed for covalent or ionic crosslinking of fenugreek gum and one or more active agents. In one embodiment, one or more crosslinking agents may be employed for covalent or ionic crosslinking of fenugreek gum and one or more synthetic or natural polymers discussed hereinabove. In a further embodiment, one or more crosslinking agents may be employed for covalent or ionic crosslinking of fenugreek gum, one or more active agents and one or more natural or synthetic polymers. In yet another embodiment, the crosslinking agent may be employed to modify the fenugreek gum prior to its use in preparation of carrier particles of the present invention. In one embodiment, the crosslinking agent may be employed to crosslink fenugreek gum and one or more synthetic or natural polymers prior to its use in preparation of carrier particles of the present invention. In another embodiment, crosslinking agent may be added during the process of preparation of carrier particles of the present invention. In a further embodiment, crosslinking agent may be added after the preparation of carrier particles of the present invention. In another embodiment, the amount of crosslinking agent present in the carrier particles of the particulate delivery system of present invention is about 0.01% to about 20% by weight of the particles. In a further embodiment, the amount of crosslinking agent present in the carrier particles of the particulate delivery system of present invention is about 0.05 to about 15% weight of the particles. In one embodiment, the amount of crosslinking agent present in the carrier particles of the particulate delivery system of present invention is about 0.1 to about 10% weight of the particles. In a further embodiment, one or more crosslinking agents may be employed during the preparation of carrier particles for various non-limiting purposes, such as, adjusting the release profile of the active agent from the carrier particles, improving the stability of the carrier particles, improving the strength of the carrier particles, improving the entrapment efficiency or drug loading of the process of preparation of carrier particles and the like.

Suitable pH modifiers that may be employed in the carrier particles of delivery systems of the present invention include, but are not limited to, organic or inorganic acids, organic or inorganic bases, buffering agents and the like or combinations thereof. Suitable organic or inorganic acids that may be employed include, but are not limited to, acetic acid, glacial acetic acid, boric acid, citric acid, hydrochloric acid, malic acid, nitric acid, phosphoric acid, propionic acid, sulfuric acid, tartaric acid, fumaric acid, lactic acid and the like or combinations thereof. Suitable organic or inorganic bases that may be employed include, but are not limited to, ammonium hydroxide, sodium hydroxide, potassium hydroxide and the like. Suitable buffering agents that may be employed include, but are not limited to, citrate, acetate, phosphate, carbonate, borate salts of sodium, potassium or ammonium and the like, pyridoxine, diethanolamine, monoethanolamine, triethanolamine, cytosine, diethylamine and the like or combinations thereof. In a further embodiment, pH modifiers and buffering agents are employed in the preparation of carrier particles of the present invention for various non-limiting purposes such as, maintaining or adjusting the pH as required during preparation of the carrier particles, altering the bonding, such as, but not limited to, hydrogen bonding amongst galactose units of adjacent galactomannan chains in fenugreek gum to reduce viscosity of the gum solution and allow easy processing into carrier particles. Examples of lipids that may be employed in the carrier particles of the present invention include, but are not limited to, fats, oils, waxes, fatty acids, fatty acid esters, glycerides, fatty alcohols, hydrogenated vegetable oil, phospholipids, terpenes and the like or combinations thereof. Suitable waxes that may be employed include, but are not limited to, natural waxes, such as animal waxes, vegetable waxes, and petroleum waxes (i.e., paraffin waxes, microcrystalline waxes, petrolatum waxes, mineral waxes), and synthetic waxes. Non-limiting examples include, but are not limited to, spermaceti wax, carnauba wax, Japan wax, bayberry wax, flax wax, beeswax, Chinese wax, shellac wax, lanolin wax, sugarcane wax, candelilla wax, paraffin wax, microcrystalline wax, petrolatum wax, carbowax, and the like, or mixtures thereof. Mixtures of these waxes with the fatty acids may also be used. Non-limiting examples of oils that may be employed include, castor oil, soyabean oil, and the like or combinations thereof. Fatty acids that may be employed in the present invention include, but are not limited to, decenoic acid, docosanoic acid, stearic acid, palmitic acid, lauric acid, myristic acid, and the like, and mixtures thereof. Suitable fatty alcohols that may be employed in the compositions of the present invention include, but are not limited to, cetyl alcohol, stearyl alcohol or mixtures thereof. Suitable hydrogenated vegetable oils that may be employed in the compositions of the present invention, include but are not limited to, hydrogenated palm kernel oil, hydrogenated peanut oil, hydrogenated palm oil, hydrogenated rapeseed oil, hydrogenated rice bran oil, hydrogenated soybean oil, hydrogenated sunflower oil, hydrogenated castor oil, hydrogenated cottonseed oil, and the like, and mixtures thereof. In one embodiment, lipids may be employed in case the carrier particles being prepared are solid lipid nanoparticles, lipid based nanoparticles or microparticles, nanoemulsions, microemulsions, liposomes, and the like or combinations thereof.

In a further embodiment, the plurality of particles in the particulate delivery systems of the present invention may further comprise active agents. Active agents such as, but not limited to, therapeutic agents, immunological agents or diagnostic agents and the like or combinations thereof may be delivered by the particulate delivery systems of the present invention.

In another embodiment, the particulate delivery systems of the present invention may include therapeutic agents belonging to the therapeutic classes such as, but not limited to, anti-cancer agents, psychostimulants, antihistamines, expectorants, mucolytics, anti-tussive agents, serotonin and norepinephrine reuptake inhibitors, sympatholytics, anti-muscarinics, PDE5 inhibitors, anti-Alzheimer's agent, analgesics, decongestants, analeptic agents, anesthetic agents, anti-asthmatics, anti-arthritic agents, anti-cholinergic agents, anti-convulsant agents, anti-depressant agents, antidiabetics, anti-helminthic agents, anti-diarrheal agents, anti-epileptics, anti-hyperlipidemic agents, antihypertensives, antihypotensives, peripheral vasodilators or vasoconstrictors, respiratory agents, anti-infective agents, anti-inflammatory agents, non-steroidal anti-inflammatory agents, anti-emetics, anti-migraine agents, anti-neoplastic agents, anti-tubercular agents, antibiotics, antacids, antiulcer agents, anti-Parkinsonism drugs, anti-pruritic agents, antipsychotic agents, antipyretic agents, anti-spasmodics, anti-viral agents, anxiolytic agents, appetite suppressants, attention deficit hyperactivity disorder treating agents, cardiovascular agents, calcium channel blockers, antianginal agents, central nervous system agents, beta-blockers; antiarrhythmic agents, bronchodilators, central nervous system stimulants, diuretics, hormonolytics, hypercalcemics, hypoglycemic agents, immunosuppressive agents, beta-agonists, narcotic antagonists, nicotine, nutritional agents, parasympatholytics, antihemorrhoidals, psychotropics, sialagogues, steroids; sympathomimetics, tranquilizers; vasodilators, hypnotics, coronary dilators, calcium antagonists, chemotherapeutic drugs, antiprotozoan drugs, alkylating agents, mitotic inhibitors, anti-metabolites, plant alkaloids, terpenoids, taxanes, topoisomerase inhibitors, camptothecins, antitumour antibiotics, hormones, steroids, gonadotropin-releasing hormone agonists, estrogen receptor binding agents, farnesyl-protein transferase inhibitors, polyphenolic agents, cytoxics, multidrug resistance modulators, radiosensitizers, antimanics, enkephalin analgesics, hallucinogenic agents, epidural and intrathecal anesthetic agents, general, local, regional neuromuscular blocking agents, sedatives, preanesthetics, anabolic steroids, dopamine agonists, growth hormone and analogs, hyperglycemic agents, lipid-altering agents, nutrients/amino acids, obesity drugs (anorectics), somatostatin, thyroid agents, vasopressin, vitamins, antiallergy, antiasthmatic agents, antiasthmatic agents (nonsteroidal), bronchoconstrictors, cough-cold-allergy preparations, corticosteroids, cathartics, cholelitholytic agents, gastrointestinal motility modifying agents, H2 receptor antagonists, irritable bowel syndrome agents, liver agents, metal chelators, gastric secretory agents, gastrointestinal drugs, drugs, pancreatitis agents, pancreatic enzymes, prostaglandins, sclerosing agents, anti-progestins, oxytocics, progestins, uterine-acting agents, anti-anemia drugs, anticoagulants, antifibrinolytics, antiplatelet agents, antithrombin drugs, coagulants, fibrinolytics, hematological agents, heparin inhibitors, blood drugs (e.g., drugs for hemoglobinopathies, hrombocytopenia, and peripheral vascular disease), anti-androgens, anti-gonorrheal agents, anti-resistant, antisepsis, dermatological agents, immunostimulatory agents, anthelmintic agents, antifungal, antimalarials, antimycobacterial, antiparasitic agents, antiprotozoal agents, radiopharmaceuticals, anti-trichomonads, antituberculosis agents, chronic fatigue syndrome, anti-HIV drugs, anti-gout drugs, cyclooxygenase inhibitors, enzyme blockers, metalloproteinase inhibitors, counterirritants, antigingivitis agents, antiplaque agents, bactericidal agents, keratolytic agents, anti-acne agents, anti-androgenic agents, chelating agents, alpha adrenergic agonists/blockers, antivirals, beta adrenergic blockers, carbonic anhydrase inhibitors, immune system regulators, mast cell inhibitors, proteolytic enzymes, 5HT3 receptor antagonists, aldosterone receptor antagonists, alpha-glucosidase inhibitors, amebicides, aminoglycosides, androgens, angiotensin converting enzyme (ACE) inhibitors, angiotensin II inhibitors, anorexiants, anti-adrenergic agents, anti-hyperuricemic agents, antibacterials, anti-psoriatics, anti-rheumatics, antiseptic and germicides, bile acid sequestrants, bisphosphonates, chemokine receptor antagonists, chloride channel activators, cholesterol absorption inhibitors, cholesterol lowering agents, cholinergic agonists, cholinesterase inhibitors, contraceptives, cox-2 inhibitors, dipeptidyl peptidase 4 inhibitors, dopaminergic agents, factor Xa inhibitors, gamma-aminobutyric acid analogs, gamma-aminobutyric acid reuptake inhibitors, pain-modulating agents, glycoprotein platelet inhibitors, *H. pylori* eradication agents, histamine receptor antagonists, impotence agents, incretin mimetics, inotropic agents, ketolides, laxatives, leukotriene modifiers, meglitinides, metabolic agents, methylxanthines, mineralocorticoids, monoamine oxidase inhibitors, mTOR kinase inhibitors, muscle relaxants, neuraminidase inhibitors, norepinephrine-dopamine reuptake inhibitors, nucleoside reverse transcriptase inhibitors (NRTIs), non-nucleoside reverse transcriptase inhibitors (NNRTIs), peripheral opioid receptor antagonists, peripheral vasodilators, peripherally acting anti-obesity agents, prolactin inhibitors, protease inhibitors, proton pump inhibitors, psychotherapeutic agents, renin inhibitors, selective serotonin reuptake inhibitors, serotoninergic neuroenteric modulators, statins, antiparasite agent, opioid, birth control agent, progestational agent, anti-glaucoma agent, ophthalmic agent, neurotoxin, muscle contractant, miotic agent, anti-secretory agent, anti-thrombotic agent, angiogenic agent, modulators of cell-extracellular matrix interactions (e.g., cell growth inhibitors and anti-adhesion molecules), anti-allergic agents, thrombin inhibitors, thrombolytics, tyrosine kinase inhibitors, antirheumatics, anti-thyroid agents, neuroleptics, cardiac inotropic agents, cough suppressants, cytotoxics, lipid regulating agents, nitrates and the like or combinations thereof may be employed.

In a further embodiment, the particulate delivery systems of the present invention may be employed to deliver one or more therapeutic agents such as, but not limited to, amphetamine, amphetaminil, atomoxetine, dexmethylphenidate, dextroamphetamine, dextromethamphetamine, fencamfamine, fenethylline, lisdexamfetamine, methylphenidate, mesocarb, pemoline, pipradrol, prolintane, dimenhydrinate, diphenhydramine, chlorpheniramine, brompheniramine, dexchlorpheniramine, hydroxyzine, dexbrompheniramine, fexofenadine, terfenadine, cetirizine, levocetirizine, fexofenadine hydrochloride or dl-chlorpheniramine maleate, ambroxol, bromhexine, carbocisteine, domiodol, guaifenesin, codeine, dextromethorphan, hydrocodone, dihydrocodeine phosphate, codeine phosphate, noscapine hydrochloride, phenylpropanolamine hydrochloride, potassium guaiacolsulfonate, cloperastine fendizoate, levocloperastine fendizoate, dextromethorphan hydrobromide, cloperastine hydrochloride, clovoxamine, desvenlafaxine, duloxetine, levomilnacipran, eclanamine, milnacipran, sibutramine, venlafaxine, alaproclate, citalopram, escitalopram, femoxetine, fluoxetine, fluvoxamine, indalpine, ifoxetine litoxetine, omiloxetine, panuramine, paroxetine, pirandamine, seproxetine, sertraline zimelidine, clonidine, guanfacine, methyldopa, iloperidone, ocaperidone, paliperidone, risperidone, lurasidone, perospirone, revospirone, tiospirone, ziprasidone, chlorpromazine hydrochloride, chlorprothexene hydrochloride, darifenacin, emepronium, fesoterodine, flavoxate, imidafenacin, meladrazine, mirabegron, oxybutynin, propiverine, solifenacin, terodiline, tolterodine, trospium chloride, acetildenafil, aildenafil, avanafil, icariin, lodenafil, mirodenafil, nitrosoprodenafil, sildenafil, selegiline, rasagiline, entacapone, tolcapone, sulfoaildenafil, tadalafil, udenafil, vardenafil, memantine, neramexane (1,3,3,5,5-pentamethylcyclohexan-1-amine), donepezil, tacrine, rivastigmine, galantamine, physostigmine, neostigmine, huperzine A, icopezil, ER-127528, zanapezil, metrifonate, FK-960, TCH-346, SDZ-220-581, tarenflurbil, tramiprosate, clioquinol, aspirin, morphine, dihydromorphine, oxycodone, alfentanil, allyprodine, alphaprodine, anileridine, benzylmorphine, bezitramide, buprenorphine, butorphanol, clonitazene, cyclazocine, desmorphine, dextromoramide, dexocine, diampromide, dimexoxadol, dimepheptanol, dimethylthiambutene, dioxaphetly butyrate, dipipanone, eptazocine, ethotheptazine, ethylmethylthiambutene, ethylmorphine, etonitazene fentanyl, fenofibrate, fenofibric acid hydromorphone, hydroxpethidine, isomethadone, ketobermidone, levallorphan, levorphanol, levophenacylmorphan, lofentanil, meperidine, meptazinol metazocine, methadone, metopon, morphine sulfate, myrophine, penicillins, nalbuphine, narceine, cicomorphine, norlevorphanol, nomethadonel nalorphine, normophine, norpipanone, ixmymorphone, papavretum, pentazocine, phenadoxone, phenmorphan, phenazocine, phenoperidine, iminodine, piritamide, propheptazine, cephalosporins, promedol, properidine, propiram, proposyphene, sufenanil, tramadol, tiline, phenylephrine, pseudoephedrine, theophylline, phenobarbital sodium, phenytoin sodium, valproate sodium barbiturates, amylobarbitone sodium, butabarbital sodium, secobarbital sodium, phenytoin, meprobamate, nitrezepam, captopril, propranolol, hydralazine hydrochloride, propranolol hydrochloride, clonidine hydrochloride, tolazoline hydrochloride, predinisolone, prednisolone sodium phosphate, albuterol, albuterol sulfate, terbutaline, naproxen, diclofenac, indomethacin, ibuprofen, sulindac, meclofenamate sodium, tolmetin sodium, metoclopramide, oleandomycin phosphate, tetracycline hydrochloride, fradiomycin, sulfate, amoxicillin, dicloxacillin sodium, pivmecillinam hydrochloride, carbenicillin indanyl sodium, atropine, scopolamine, scopolamine hydrobromide, metixene hydrochloride, dicyclomine hydrochloride, dl-methylephedrine hydrochloride, dl-methylephedrine saccharinate; ethacrynic acid, bendrofluazide, nifedipine, papaverine, diltiazem, nicardipine, chlordiazepoxide hydrochloride, diazepam, alprazolam, imipramine hydrochloride, risperidone, sertraline hydrochloride, paroxitene hydrochloride, venlafaxine hydrochloride, sodium salicylate, etafenone hydrochloride, verapamil hydrochloride, sulfisomidine sodium, kanamycin sulfate, amodiaquine hydrochloride, dl-methyl-ephedrine hydrochloride, dehydrocholic acid, diflunisal, fenoprofen, furosemide, gemfibrozil, progencid, salicylic acid, acetylsalicylic acid, acetophenazine, amitriptyline, benztropine, biperiden, bromodiphenhydramine, carbinoxamine, chloperastine, chlorcyclizine, chorpheniramine, chlorphenoxamine, chlorpromazine, clemastine, clomiphene, cyclizine, cyclobenzaprine, cyproheptadine, desipramine, dicyclomine, diphemanil, doxepin, doxylamine, ergotamine, fluphenazine, haloperidol, hydroxychloroquine, hyoscyamine, levopropoxyphene, maprotiline, meclizine, mepenzolate, meperidine, mephentermine, mesoridazine, metformin, methylepherdine, methdilazine, methscopolamine, methysergide, metoprolol, nortriptylene, noscapine, nylindrin, oxymorphone, orphenadrine, phendimetrazine, phentermine, phenylpropanolamine, pyrilamine, tripelennamine, triprolidine, promazine, propoxyphene, propanolol, quinidine, aminocaproic acid, aminosalicylic acid, isoxurprine, melphalan, nalidixic acid, paraaminosaliclic acid, chlorpheniramine, niacin, methylphenidate hydrochloride, dexmethylphenidate hydrochloride, oxymorphone hydrochloride, hydrocodone bitartrate, albuterol sulfate, albuterol phosphate, chlorpheniramine maleate, metformin hydrochloride, oxybutynin hydrochloride, saligenine hydrochloride, cetrizine hydrochloride, ranitidine hydrochloride, nitrosoureas cisplatin, carboplatin, oxaliplatin, mechlorethamine, cyclophosphamide, chlorambucil, vincristine, vinblastine, vinorelbine, vindesine, podophyllotoxin, teniposide, docetaxel, irinotecan, topotecan, amsacrine, dactinomycin, dexamethasone, tamoxifen, goserelin, paclitaxel, doxorubicin, daunorubicin, mitomycin, actinomycin D, bleomycin, tumor necrosis factor, taxol, carmustine, busulfan, lomustine, 5-fluorouracil, anthocyanin, capecitabine, gemcitabine, idarubicin, ifosfamide, lapatinib, lectrozole, navelbine, parthenolide, plicomycin, procarbazine, raloxifene, temazolomide, transplatinum, and methotrexate, etoposide, SN-38, aluminum chloride, aluminum chlorohydrate, aluminum chlorohydrex compounds, aluminum dichlorohydrate, aluminum dichlorohydrex compounds, aluminum sesquichlorohydrate, aluminum sesquichlorohydrex compounds, aluminum zirconium tetrachlorohydrex gly, aluminum zirconium trichlorohydrex gly, ammonium alum, aluminum sulfate compounds, aluminum zirconium compounds, terbinafine, clotrimazole, econazole, selenium sulfide, benzoyl peroxide, triclosan, chlorhexidine gluconate, erythromycin, clindamycin, spironolactone, cortisone, topical retinoid, tretinoin, adapalene, tazarotene, retinal, isotretinoin, oral retinoids, retinoic acids, aloe vera, aruna, turmeric, papaya, azelaic acid, rofecoxib, nicotinamide, vitamin B3, tea tree oil, aminolevulinic acid, azithromycin, methylaminolevuninate, nadifloxacine, PRK124, talarozole, zileuton, zinc, minoxidil, finasteride, dutasteride, ketoconazole, fluconazole, saw palmetto, caffeine, unsaturated fatty acids, gamma linolenic acid, hedgehog agonists, chinese knotweed, pumpkin seed, stinging nettle, aldara, alefacept, AS101, bimatoprost, capsaicin, efalizumab, FK506, GP 11046, GP11511, hydroxychloroquine, latanoprost, MK0906, roxithromycin, tetrapeptide aldehyde proteasome inhibitor (e.g., NEOSH 101, etc.), carbohydrates, lipids, organometallic compounds, radioactive elements, metals and compounds, norfloxacin, tinidazole, sirolimus, aprepitant, danazol, piposulfam, piposulfan, amiodarone, amlodipine, astemizole, atenolol, azathioprine, azelatine, beclomethasone, budesonide, butalbital, carbamazepine, carbidopa, cefotaxime, cephalexin, cholestyramine, ciprofloxacin, cisapride, clarithromycin, clonazepam, clozapine, cyclosporin, diazepam, digoxin, dipyridamole, divalproex, dobutamine, doxazosin, enalapril, estradiol, etodolac, famotidine, felodipine, flunisolide, flurbiprofen, glipizide, gliburide, isosorbide dinitrate, Isradipine, itraconazole, ketoprofen, lamotrigine, lansoprazole, loperamide, loratadine, lorazepam, lovastatin, medroxyprogesterone, mefenamic acid, methylprednisolone, midazolam, mometasone, nabumetone, nicergoline, omeprazole, phenytoin, piroxicam, quinapril, ramipril, simvastatin, triamcinolone, valproic acid, zolpidem, isoflavone, montanide isa, spiramycin, fluorouracil, busulphan, nabumetone, acetaminophen, phenacetin, 5-aminosalicylates and the like or combinations thereof in the form of free base or acid or pharmaceutically acceptable salts, prodrugs, active metabolites, polymorphs, solvates, hydrates, derivatives, enantiomers, optical isomers, tautomers or racemic mixtures thereof. In a further embodiment, the therapeutic agents employed may be, but not limited to, cationic, anionic or amphoteric in nature. In another embodiment, the therapeutic agents employed may be hydrophobic, or hydrophilic in nature.

In a further embodiment, in addition to the above, therapeutic agents of biotechnological type such as, but not limited to, proteins, antibodies, protein complexes, botulinum toxin, nucleic acids, polypeptides, multimeric proteins, glycoproteins, hormones, and the like or combinations thereof may be delivered by the particulate delivery systems of the present invention. In another embodiment, nucleic acid that may be employed includes, but is not limited to, oligonucleotides, polynucleotides, RNA, single and/or double-stranded DNA, cDNA, nucleotide sequences that encode proteins and/or RNA optionally may include introns, nucleic acid segment comprising at least 3, 4, 5, 6, 7, 8, 9, 10, or more residues, nucleosides such as, but not limited to, adenosine, thymidine, guanosine, cytidine, uridine, deoxyadenosine, deoxythymidine, deoxyguanosine, deoxycytidine, nucleoside analogs, such as, but not limited to, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine and the like or combinations thereof; chemically modified bases; biologically modified bases such as methylated bases; intercalated bases; modified sugars (e.g., Z-fluororibose, ribose, 2'-deoxyribose, arabinose, and hexose); and/or modified phosphate groups (e.g., phosphorothioates and 5'-N-phosphoramidite linkages) and the like or combinations thereof; DNA-RNA hybrids, siRNAs, shRNAs, miRNAs, RNAi-inducing entities, aptamers, modified backbones, non-naturally occurring internucleoside linkages; interleukins, interferon, cytokines, modified oligonucleotide (including, but not limited to, modifications through phosphorylation); an antisense oligonucleotide and/or modified antisense oligonucleotide (including, but not limited to, modifications through phosphorylation), cDNA and/or genomic DNA, non-human DNA and/or RNA (e.g., viral, bacterial, or fungal nucleic acid sequences), plasmid, cosmid, gene fragment, artificial and/or natural chromosome (e.g., a yeast artificial chromosome), functional RNA (e.g., mRNA, a tRNA, an rRNA and/or a ribozyme), peptide nucleic acid (PNA), polynucleotide comprising synthetic analogues of nucleic acids, which may be modified or unmodified; nucleic acid modifications to reduce and/or prevent digestion by nucleases (e.g., exonucleases, endonucleases, etc.) and the like or combinations thereof. In another embodiment, modified nucleotides that may be employed includes, but is not limited to base modified nucleoside such as, but not limited to, aracytidine, isoguanosine, nebularine, pseudouridine, 2,6-diaminopurine, 2-aminopurine, 3-deaza-5-azacytidine, 2'-deoxyuridine, 3-nitorpyrrole, 4-methylindole, 4-thiouridine, A-thiothymidine, 2-thiouridine, 5-bromocytidine, 5-iodouridine, 6-azauridine, 6-chloropurine, 7-deazaadenosine, 7-deazaguanosine, 8-azaadenosine, 8-azidoadenosine, benzimidazole, MI-methyladenosine, pyrrolo-pyrimidine, 2-amino-6-chloropurine, 2'-aminoribose, 2'-azidoribose, T-O-methylribose, L-enantiomeric nucleosides arabinose, and hexose; modified phosphate groups, such as, but not limited to, phosphorothioates and 5'-iV-phosphoramidite linkages; and the like or combinations thereof. In one embodiment, some biotechnological agents may be used as ligands for targeting specific biological tissues.

In another embodiment, the particulate delivery systems of the present invention may include immunological agents such as, but not limited to, vaccines. In a further embodiment, vaccines that may be delivered by the particulate delivery systems of the present invention include, but are not limited to, isolated proteins or peptides, inactivated organisms and viruses, dead organisms and virus, genetically altered organisms or viruses, cell extracts, antigens, antigens of bacterial organisms, such as, but not limited to, *Streptococccus pnuemoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae,*

*Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of viruses such as, but not limited to, smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as, but not limited to, *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like; antigens in the form of whole killed organisms, peptides, proteins, glycoproteins, carbohydrates, or combinations thereof; optionally combined with interleukins, interferon, cytokines, or adjuvants such as, but not limited to, alum, Freund's adjuvant; and the like or mixtures thereof.

In a further embodiment, the particulate delivery systems of the present invention may include diagnostic agents such as, but not limited to, magnetic resonance image (MRI) enhancement agents or imaging agents, positron emission tomography products, radioactive diagnostic agents, radioopaque contrast agents, ultrasound imaging agents, angiographic diagnostic agents, dyes and radioisotopes (e.g. P32, Tc99, F18, I131 and the like); and the like or combinations thereof. Suitable magnetic resonance image (MRI) enhancement agent or MR imaging agent includes, but is not limited to, gadolinium-diethylenetriaminepentaacetic acid complex, metal chelate, such as, but not limited to, a chelating ligand and a paramagnetic metal ion coordinated thereto with non-limiting examples of chelating ligand being cyclic and acyclic chelating ligands such as, but not limited to, DTPA, DOTA, DOTMA, DTPA-BMA, DOTAGA, and HP-DO3A, and non-limiting examples of paramagnetic metal ions are Gd(III), Fe(III), Mn(II), Cr(III), Cu(II), Dy(III), Ho(III), Er(III), Eu(III), Tb(II), Tb(III), and Tb(IV) and the like or combinations thereof.

In one embodiment, one or more active agents may be delivered by particulate delivery systems of the present invention. In a further embodiment, one or more active agents may be adsorbed, dissolved or dispersed throughout the matrix of carrier particles of the particulate delivery systems of the present invention comprising fenugreek gum. In another embodiment, one or more active agents may be encapsulated within the carrier particles of the particulate delivery systems of the present invention comprising fenugreek gum. In yet another embodiment, one or more active agents may be attached to the surface of the carrier particles of the particulate delivery systems of the present invention comprising fenugreek gum. In one embodiment, one or more active agents may be covalently attached to the surface of the carrier particles of the particulate delivery systems of the present invention comprising fenugreek gum. In yet another embodiment, one or more active agents may be ionically attached to the surface of the carrier particles of the particulate delivery systems of the present invention comprising fenugreek gum. In a further embodiment, particulate delivery systems of the present invention may comprise one or more active agents adsorbed, dispersed, or dissolved throughout the matrix of carrier particles or encapsulated within the carrier particles or attached or adsorbed onto the surface of the carrier particles and one or more active agents in free non-particulate form. In another embodiment, particulate delivery systems of the present invention may comprise part dose of one or more active agents adsorbed, dispersed, or dissolved throughout the matrix of carrier particles or encapsulated within the carrier particles or attached or adsorbed onto the surface of the carrier particles and remaining dose of the same one or more active agents in free non-particulate form. In one embodiment, one or more active agents in, but not limited to, solid, liquid, semisolid, or solubilized form may be included in the carrier particles of the particulate delivery system of the present invention. In one embodiment, one or more active agents may be solubilized with the use of at least one solubilizer selected from, but not limited to, surfactants, cyclodextrins, hydrophilic polymers, lipids, pH modifiers and the like or combinations thereof. Suitable surfactants as listed herein above may be employed for solubilization. In another embodiment, active agents included in the delivery systems of the present invention may be water-soluble or water-insoluble in nature. In a further embodiment, active agents with an aqueous solubility of about 10 µg/ml to 200 mg/ml may be delivered by the particulate delivery system of the present invention. In one embodiment, the aqueous solubility may be determined by the method of United State Pharmacopoeia (USP) 34. In another embodiment, active agents included in the delivery systems of the present invention may be hydrophilic or hydrophobic in nature. In a further embodiment, one or more active agent may be acidic, basic or neutral in nature.

Pharmaceutically effective amount of active agent is employed in the composition of the present invention. The term "effective amount" refers to an amount effective to achieve desired preventive, therapeutic, immunological, diagnostic and/or beneficial effect. In one embodiment the amount of active agent in the composition can vary from about 0.01 weight % to about 85 weight %, based on the total weight of the composition. In another embodiment the amount of active agent in the composition can vary from about 0.02 weight % to about 80 weight %, based on the total weight of the composition. In still another embodiment, the amount of active agent in the composition can vary from about 0.05 weight % to about 75 weight %, based on the total weight of the composition.

As discussed herein above, carrier particles incorporated in the delivery systems of the present invention include, but are not limited to, nanoparticles, nanospheres, nanocapsules, microparticles, microspheres, microcapsules, liposomes, nanoemulsions, solid lipid nanoparticles, and the like or mixtures thereof. In a further embodiment, the carrier particles present in the particulate delivery systems of the present invention may be prepared by methods, such as, but not limited to, nanoprecipitation, emulsion solvent evaporation method, emulsion-crosslinking method, emulsion solvent diffusion method, microemulsion method, gas antisolvent precipitation method, ionic gelation methods milling or size reduction method, PEGylation method, salting-out method, dialysis method, single or double emulsification method, nanospray drying method, layer by layer method, desolvation method, supercritical fluid technology, and the like or any combinations thereof.

In one embodiment, the carrier particles of the particulate delivery system of the present invention are prepared by emulsion-solvent evaporation method. In a further embodiment, the emulsion solvent evaporation method comprises the first step of emulsification of the gum solution, followed by the evaporation or removal of the gum solvent, causing precipitation of the gum as nanoparticles, nanospheres, microparticles, or microspheres. In a further embodiment, water immiscible organic solvent is employed in the process. In one embodiment, one or more active agent/s may be included in one or both of the phases of the emulsion being prepared. In a further embodiment, the gum solution may be prepared in solvents, such as, but not limited to, water, pH7.4 phosphate buffer, and the like. In another embodiment, one or more surfactants, or surface modifiers may be included in one or both the phases. In one embodiment, in emulsion-crosslinking method, one or more cross linking agents may be added in one or both the phases. In a further embodiment, the resulting carrier particles may be collected by ultracentrifugation and washed with distilled water and lyophilized for storage. In a further embodiment, the active agent may be entrapped, dispersed, or dissolved in the carrier particles. In another embodiment, the active agent is not included in any of the emulsion phases, but is attached covalently or ionically to the nanoparticles, nanospheres, microparticles, microspheres or the like prepared or is incubated with these carrier particles for adsorption of the active agent/s on the particle surface. In yet another embodiment, the emulsion prepared as discussed hereinabove may be subjected to homogenization under high pressure followed by removal of the solvent to further reduce the size of the carrier particles. In a further embodiment, the size of the carrier particles of particulate systems prepared by this method can be controlled by adjusting the stirring rate, type and amount of surfactant, viscosity of organic and aqueous phases and temperature.

In another embodiment, carrier particles of the particulate delivery systems of the present invention are prepared by double emulsion technique. In one embodiment, the double emulsion technique involves the preparation of w/o emulsions comprising the active agent and the gum or only the gum in either of the phases. In a further embodiment, this mo emulsion is added into second aqueous phase with continuous stirring to form the w/oiew emulsion. The final emulsion is then subjected to solvent removal by evaporation and the resulting nanoparticles or microparticles are isolated. In a further embodiment, the nanoparticles or microparticles formed are separated by centrifugation at high speed and thoroughly washed before lyophilization. Suitable crosslinking agents, surfactants, solvents, and the like may be employed for the preparation of carrier particles by the method discussed above. In one embodiment, the size and entrapment efficiency of nanoparticles are controlled by various factors such as, but not limited to, the concentration of surfactants or other excipients used, the gum concentration, the volume of aqueous phase and the like. In one embodiment, the gum solution may be prepared in solvents, such as, but not limited to, water, pH7.4 phosphate buffer, and the like. In a further embodiment, the active agent may be incorporated during the formation of the carrier particles. In another embodiment, the carrier particles may be treated with the active agent after their formation. In a further embodiment, one or more active agents may be physically adsorbed or chemically or ionically attached to the carrier particles.

In another embodiment, the carrier particles of the particulate delivery system of the present invention are prepared by emulsion solvent diffusion method. In one embodiment, the emulsion solvent diffusion method involves the use of partially water miscible organic solvents, such as, but not limited to, benzyl alcohol, propylene carbonate, ethyl acetate and the like. In one embodiment, fenugreek gum alone or fenugreek gum and the active agent are dissolved in aqueous phase, such as but not limited to, water, pH 7.4 phosphate buffer, and the like, and this phase is added under continuous stirring to the partially water-miscible organic solvent. In one embodiment, mechanical stirring or high pressure homogenization may be employed. In a further embodiment, carrier particles are formed by diffusion of the organic solvent and the counter diffusion of water into the emulsion droplets. In another embodiment, the solvent is removed by evaporation or cross-flow filtration. In one embodiment, the carrier particles are recovered by centrifugation and finally dried in a vacuum oven. In another embodiment, the resulting carrier particles may be collected by ultracentrifugation, washed with distilled water and lyophilized for storage. In a further embodiment, during the preparation of carrier particles, one or more active agents, surfactants, surface modifiers or crosslinking agents may be added in the aqueous or partially water miscible organic solvent phase. In a further embodiment, gum concentration, amount of surfactant, miscibility of water with the organic solvent and stirring rate are the key process parameters that need to be considered while preparing carrier particles by this method.

In another embodiment, partially water miscible organic solvents may be added to the aqueous phase. In one embodiment, fenugreek gum or modified fenugreek gum may be dissolved in the organic solvent phase. In one embodiment, one or more active agents may be included in one or both of the phases of the emulsion being prepared. In a further embodiment, the active agent may be entrapped, dispersed, or dissolved in the carrier particles. In another embodiment, the active agent is not included in any of the emulsion phases, but is attached covalently or ionically to the nanoparticles, nanospheres, microparticles, microspheres or the like prepared or is incubated with these carrier particles for adsorption of the active agent's on the particle surface.

In another embodiment, the carrier particles of particulate delivery systems of the present invention are prepared by nanoprecipitation method or solvent displacement method or precipitation-solvent evaporation method. In one embodiment, water miscible solvent, such as, but not limited to, acetone, ethanol, dimethyl sulfoxide, isopropyl alcohol or the like, is employed in this method as a gum solvent or antisolvent depending upon the nature of the gum, particularly if the gum has been modified. In a further embodiment, gum and optionally the active agent is dissolved in aqueous phase, such as, but not limited to, water, pH7.4 phosphate buffer, and the like and the solution is injected or poured into organic antisolvent/s under continuous stirring. In another embodiment, one or more active agents, surfactants, surface modifiers, or cross-linking agents may be incorporated in either the organic or aqueous phases during the process of preparation of the carrier particles. In a further embodiment, the rapid diffusion of gum solvent in the antisolvent or nonsolvent leads to the instantaneous formation of carrier particles. In one embodiment, the gum solution may be prepared in the organic solvent and aqueous phase or water may be the antisolvent. In another embodiment, the gum solvent is removed by either evaporation or centrifugation, and carrier particles are washed and lyophilized. In another embodiment, the nature of the gum, particularly modified gum, gum concentration, surfactant or surface modifier type and concentration, solvent nature, viscosity and nature of the active agent are the main factors to be considered. In one embodiment, in the nanoprecipitation method the antisolvent employed leads to displacement of one phase by the other to form colloidal suspension comprising the gum, which when agitated leads to formation of carrier particles of the present invention. In one embodiment, one or more active agent's may be included in one or both of the phases of the suspension being prepared. In a further embodiment, the precipitation-solvent evaporation method comprises mixing gum solution comprising one or more crosslinking agents with a volatile antisolvent continuously with high pressure homogenization, followed by evaporation of the antisolvent leading to precipitation of the gum as nanoparticles, nanospheres, microparticles, or microspheres. In one embodiment, one or more active agent's may be included in one or both of the solutions employed in the process of preparation. In a further embodiment, the resulting carrier particles may be collected by ultracentrifugation and washed with distilled water and lyophilized for storage. In a further embodiment, the active agent may be entrapped, dispersed, or dissolved in the carrier particles. In another embodiment, the active agent is not included in any of the emulsion phases, but is attached covalently or ionically to the nanoparticles, nanospheres, microparticles, microspheres or the like prepared or is incubated with these carrier particles for adsorption of the active agent's on the particle surface.

In yet another embodiment, the carrier particles of particulate delivery system of the present invention are prepared by desolvation method. In one embodiment, the desolvation method comprises adding a suitable desolvating agent to gum solution under stirring till the solution becomes turbid, adding resolvating agent, if required, optionally, followed by addition of a cross-linking agent and subsequent solvent evaporation resulting in the formation of nanoparticles, nanospheres, microparticles, or microspheres of gum. The resulting carrier particles may be separated by filtration and kept for drying. In a further embodiment, the size of the carrier particles may be controlled by adjusting the pH of the solution with pH modifiers and the rate of addition of desolvating agent to the gum solution. In one embodiment, the desolvating agents can be added to the gum solution continuously at a predetermined rate with fixed time interval. In yet another embodiment, the desolvating agent can be added to the gum solution intermittently with a predetermined time gap. In another embodiment, a homogenizer may also be employed to reduce the size of the carrier particles. In one embodiment, suitable solvents listed herein above may be employed as desolvating or resolvating agents depending on the solvent used for preparing the gum solution and type of active agent to be delivered. In a further embodiment, one or more active agent's may be included in gum solution or desolvating agent. In another embodiment, one or more active agent's may be included in both the gum solution and desolvating agent. In a further embodiment, the active agent may be entrapped, dispersed, or dissolved in the carrier particles. In another embodiment, the active agent is not included in any of the solutions/solvents employed during the preparation, but is attached covalently or ionically to the nanoparticles, nanospheres, microparticles, microspheres or the like prepared or is incubated with these carrier particles for adsorption of the active agent's on the particle surface.

In yet another embodiment, the carrier particles of particulate delivery system of the present invention are prepared by microemulsion method. In one embodiment, the microemulsion method comprises of adding solution of surfactant in organic solvent to gum solution containing a crosslinking agent under continuous vigorous stirring or homogenization at room temperature leading to the formation of crosslinked carrier particles comprising the gum. These resulting crosslinked carrier particles may be collected by evaporation of the organic solvent under reduced pressure. In another embodiment, the carrier particles were further purified by addition of complexing agents to remove excess surfactant, followed by centrifugation to remove the carrier particles, dialysis with distilled water and lyophilization for storage. In one embodiment, the size of the carrier particles depends on various factors, such as but not limited to, stirring rate, type and concentration of surfactant, and type of organic solvent employed. In a further embodiment, one or more active agents may be included in one or both of the gum solution or surfactant solution. In a further embodiment, the active agent may be entrapped, dispersed, or dissolved in the carrier particles. In another embodiment, the active agent is not included in any of the emulsion phases, but is attached covalently or ionically to the carrier particles or is incubated with these carrier particles for adsorption of the active agent's on the particle surface.

In one embodiment, the carriers of present application may be prepared by salting out method which comprises of formation of emulsion by mixing gum solution in a suitable solvent and a solution comprising surfactant and a salting out agent in a suitable solvent under vigorous mechanical stirring, followed by dilution with sufficient volume of the solvent of the salting out agent which enhances the diffusion of the gum solvent out of the emulsion droplets leading to formation of nanoparticles, nanospheres, microparticles, or microspheres of the gum. In a further embodiment, the resulting carrier particles may be further purified by elimination of solvent and salting out agents by cross flow filtration. In one embodiment, salting out agent is present in the continuous phase of the emulsion formed. In another embodiment, the salting out method involves formation of oil/water (o/w) emulsion, with the emulsion being formed from water-miscible polymer solvent and aqueous gel comprising at least one salting out agent and at least one surfactant or surface modifier. Suitable salting out agents depending on the solvent used for the gum may be employed, such as, but not limited to, electrolytes, non-electrolytes and the like or combinations thereof. Suitable electrolytes that may be used as salting out agents, include, but are not limited to, magnesium chloride, calcium chloride, sodium chloride, magnesium acetate, and the like or combinations thereof. Suitable non-electrolytes that may be used as salting out agents, include, but are not limited to, sucrose, saccharose and the like or combinations thereof. In another embodiment, the salting out agents for acetone are the various electrolytes, such as but not limited to, magnesium chloride, calcium chloride etc. In one embodiment, the salting out method may be employed when using modified fenugreek gum. In a further embodiment, the physicochemical properties of the carrier particles produced by this process are affected by various factors such as, but not limited to, gum concentration, stirring rate and time, solvent type and nature of salting out agent. In another embodiment, one or more active may be included in one or both of the gum solution or surfactant solution. In a further embodiment, the active agent may be entrapped, dispersed, or dissolved in the carrier particles. In another embodiment, the active agent is not included in any of the emulsion phases, but is attached covalently or ionically to the nanoparticles, nanospheres, microparticles, microspheres or the like prepared or is incubated with these carrier particles for adsorption of the active agent's on the particle surface.

In further embodiment, carrier particles of the present invention may be prepared by polyelectrolyte complexation method. In another embodiment, the carrier particles may be prepared by complex formation between oppositely charged polyelectrolytes and fenugreek gum. In one embodiment, polyelectrolyte complexes are formed due to electrostatic interaction between oppositely charged polyelectrolytes and gum. In a further embodiment, carrier particles may be prepared by complex formation between, but not limited to, oppositely charged synthetic or natural polymer and fenugreek gum, oppositely charged fenugreek gum and one or more active agent, or oppositely charged synthetic or natural polymer, fenugreek gum and one or more active agent and the like or combinations thereof. In a further embodiment, fenugreek gum may be modified to acquire the desired charge for polyelectrolyte complex formation. In another embodiment, fenugreek gum may be solubilized or dispersed in a solvent wherein it may acquire the desired charge for polyelectrolyte complex formation. In one embodiment, fenugreek gum may be made to acquire the desired charge for polyelectrolyte complex formation by any method known in the art for the same. In one embodiment, carrier particles prepared by polyelectrolyte complexation method may not include one or more crosslinking agents discussed herein above. In another embodiment, carrier particles prepared by polyelectrolyte complexation method may include one or more crosslinking agents. In an embodiment, one or more crosslinking agents may be added to either or both the oppositely charged polyelectrolyte or fenugreek gum solutions before complexation. In another embodiment, one or more crosslinking agents may be added during the process of polyelectrolyte complex formation between oppositely charged polyelectrolytes and fenugreek gum. In a further embodiment, one or more crosslinking agents may be added after polyelectrolyte complex formation.

In a further embodiment, depending on a variety of factors, such as, but not limited to, the chemical composition of the polymers, the concentrations of the polyelectrolytes, their mixing ratio, ionic strength of the solution, mixing order, and the like, the polyelectrolyte complexation method may cause the system to separate into a dilute phase and a concentrated complex coacervate phase, or it may result in a more-or-less compact precipitate or gel, or the complexes may also remain in solution. In one embodiment, the resulting carrier particles may be separated by centrifugation and separation from the solvent. In one embodiment, oppositely charged gum solution and polyelectrolyte solution may be mixed in a molar ratio of 1:99 to 99:1. In one embodiment, one or more active agent's may be included in one or both of the polyelectrolyte and fenugreek gum solutions. In a further embodiment, the active agent may be entrapped, dispersed, or dissolved in the carrier particles. In another embodiment, the active agent is not included in any of the solutions, but is attached covalently or ionically to the carrier particles or is incubated with these carrier particles for adsorption of the active agent's on the particle surface.

In a further embodiment, the carrier particles of the present invention may be prepared by coacervation method. In one embodiment, coacervation method involves electrostatically-driven liquid-liquid phase separation into colloid-poor and colloid-rich (coacervates) phases, resulting from association of oppositely charged macro-ions including fenugreek biopolymer. In one embodiment, fenugreek gum or biopolymer may be appropriately modified to have desired cationic, anionic or amphoteric nature for preparation of carrier particles by coacervation method. In a further embodiment, carrier particles of the present invention may be prepared by coacervation method using modified fenugreek gum. In one embodiment, the carrier particles of the present invention in the form of coacervates may be prepared by electrostatic interaction of modified gum with the oppositely charged synthetic or natural polymers or oppositely charged fenugreek gum itself, under mechanical stirring at room temperature. In a further embodiment, the modified gum solution is mixed with solution of oppositely charged synthetic or natural polymer or oppositely charged fenugreek gum itself under stirring leading to the formation of coacervates of carrier particles of present invention in the colloid rich phase. In another embodiment, the resulting carrier particles are further collected from the colloid rich phase, washed with distilled water and stored. In one embodiment, surfactants may be added to either of the solutions discussed above. In yet another embodiment, the surfactants may be added after the addition of modified gum solution to the oppositely charged synthetic or natural polymer solution or vice versa. In yet another embodiment, the one or more active agents may be included in one or both of the solutions discussed hereinabove. In a further embodiment, the active agent may be entrapped, dispersed, or dissolved in the carrier particles. In another embodiment, the active agent is not included in any of the above phases, but is attached covalently or ionically to the carrier particles prepared or incubated with these carrier particles for adsorption of the active agent's on the particle surface.

In a further embodiment, the carrier particles of present invention can be prepared by interaction of fenugreek gum and one or more surfactants by adjusting the pH of the mixture of the solutions and subjecting the mixture of the solutions to a wide range of temperature. In one embodiment, the mixture of the gum solution and surfactant solution was subjected to high temperature followed by quenching to room temperature leading to formation of colloidal dispersion of aggregated gum. In one embodiment, the aggregates of gum may further be treated with cross-linking agent. In yet another embodiment, the crosslinking agent may be added in one of the solutions or after the formation of aggregates of gum in the mixture of the solutions. In a further embodiment, aggregated gum may be used as carrier particles of the present invention. In one embodiment, one or more active agent's may be included in one or both of the solutions used for the preparation of carrier particles. In a further embodiment, the active agent may be entrapped, dispersed, or dissolved in the carrier particles. In another embodiment, the active agent is not included in any of the solutions, but is attached covalently or ionically to the carrier particles or is incubated with these carrier particles for adsorption of the active agent's on the particle surface. In one embodiment, the fenugreek gum solution may be mixed with one or more natural or synthetic polymer solution vigorously under high temperature for some time and the carrier particles may be precipitated by evaporation of solvent. In another embodiment, polyethylene glycol may be used as a polymer solution which may lead to formation of pegylated carrier particles. In another embodiment, PEGlayted fenugreek gum may be employed in the preparation of carrier particles of the present invention.

In a further embodiment, the carrier particles prepared by any of the above processes may be functionalized. In another embodiment, the carrier particles prepared by any of the above processes may be functionalized with molecules such as, but not limited to, polyethylene glycol (PEGs), biological molecules that can act as address tags, to direct the nanoparticles to specific sites within the body, specific organelles within the cell or to follow specifically the movement of individual protein or RNA molecules in living cells, such as, but not limited to, monoclonal antibodies, aptamers, streptavidin or peptides and the like or combinations thereof. In a further embodiment, the carrier particles of the particulate delivery system of the present invention may be conjugated to synthetic or natural polymers.

In a further embodiment, the size and shape of the carrier particles of the present invention prepared by any of the methods described hereinabove may be evaluated by methods, such as but not limited to, scanning electron microscopy and the like. In another embodiment, the particle size and size distribution analysis of the carrier particles of the present invention prepared by any of the methods as described hereinabove may be done by using, but not limited to, laser diffraction particle size analyzer and like. In one embodiment, evaluation of non-aggregation of carrier particles may be carried out by methods, such as, but not limited to, turbidometry, scanning electron microscopy, dynamic light scattering technique, transmission electron microscopy and the like. In a further embodiment, the drug-loading capacity and encapsulation efficiency of the carrier particles of the present invention prepared by any of the methods as described hereinabove may be determined by, but not limited to, ultrasonication and centrifugation of formulation and analysis of active drug concentration in the supernatant using HPLC or by determining in-vitro dissolution profile and the like. In a further embodiment, the in-vitro release profile of active agent comprising fenugreek based carrier particles prepared by any of the processes described hereinabove may be carried out by, but not limited to, dissolution method and the like.

In a further embodiment, the particulate delivery system of present invention can be administered by various routes such as, but not limited to, oral, transdermal, topical, inhalation, intranasal, buccal, sublingual, rectal, vaginal, enteral, transmucosal, pulmonary, ocular, parenteral (e.g. intramuscular, subcutaneous, intraperitoneal, intratumoral, intravenous, intraarterial, intramedullary, intrathecal, intraventricular, intracranial, intravaginal, intrapulmonary, intraocular, intrarectal, interdermal, or intradermal) and the like. In one embodiment, the particulate delivery system of the present invention can be administered by oral, topical, or parenteral routes.

In another embodiment, depending on the route of administration, the particulate delivery systems of the present invention may be delivered in the form of, but not limited to, tablets, granules, capsules, pills, pellets, suspensions, emulsions, linctuses, mouthwashes, gargles, nanoemulsion, nanosuspensions, nanogel, caplets, enteric coated tablets, enteric coated capsules, effervescent tablet, orally disintegrating tablets, dispersible tablets, dry suspension for reconstitution, wafers, bite-dispersion tablets, gastroretentive nanospheres, poultice, pastes, dusting powders, liniments, creams, lotions, gels, ointments, drops, shampoo, conditioner, sunscreen, deodorant, antiperspirant (e.g. as a roll-on, solid stick), suppositories, enemas, aerosol, powder, face wash, body wash, eye drops, ocular creams, ocular ointments, dry powder for inhalation, solutions, nasal sprays, and the like. In one embodiment, the particulate delivery system of the present invention for oral administration may be in the form of liquid, semi-solid or solid dosage form. In a further embodiment, the particulate delivery system of the present invention for parenteral administration may be in the form of, but not limited to, aqueous sterile suspensions or nanosuspensions, non-aqueous sterile suspensions or nanosuspensions, aqueous sterile solutions, non-aqueous sterile solutions and the like.

In a further embodiment, depending on the route of administration and the final dosage form, the carrier particles comprising fenugreek gum may be incorporated in a suitable delivery vehicle to prepare the particulate delivery system of the present invention. In one embodiment, the particulate delivery system of the present invention comprises (a) plurality of particles comprising fenugreek gum and at least one pharmaceutically acceptable excipient and (b) delivery vehicle. In another embodiment, the particulate delivery system of the present invention comprises (a) plurality of particles comprising fenugreek gum, one or more active agents and at least one pharmaceutically acceptable excipient and (b) delivery vehicle. In one embodiment the particulate delivery system of the present invention may comprise only plurality of particles comprising fenugreek gum and at least one pharmaceutically acceptable excipient. In another embodiment, the particulate delivery system of the present invention may comprise only plurality of particles comprising fenugreek gum, one or more active agent and at least one pharmaceutically acceptable excipient. In another embodiment, the delivery vehicle of the particulate delivery systems of the present invention may comprise at least one pharmaceutically acceptable excipient, such as, but not limited to, disintegrants, superdisintegrants, lubricants, glidants, binders, diluents, salivating agents, surfactants, tonicity adjusting agents, cryoprotectants, penetration enhancers, waxes and oils, propellants, preservatives, flavors, sweeteners, colorants, viscosity modifying agents, plasticizers, neutralizing agents, souring agents, thickening agents, humectants, emollients, antioxidants, pH modifiers, gelling agents, solvents, and the like or any combinations thereof.

Suitable disintegrants that may be employed include, but not limited to, croscarmellose sodium, crospovidone, calcium silicate, sodium starch glycolate, starch and the like or combinations thereof. Suitable superdisintegrants that may be employed include, but are not limited to, natural, modified or pregelatinized starch, crospovidone, croscarmellose sodium, sodium starch glycolate, low-substituted hydroxypropyl cellulose and the like or combinations thereof. Suitable lubricants that may be employed include, but are not limited to, talc, silica, calcium stearate, stearic acid, sodium stearyl fumarate, magnesium stearate and the like or combinations thereof. Suitable glidants that may be employed include, but are not limited to, talc, colloidal silica, silica gel, precipitated silica, and the like or combinations thereof. Suitable binders that may be employed include, but are not limited to, starch, sorbitol, polyvinylpyrollidone, cellulose, cellulose derivatives, such as, such as, but not limited to, hydroxypropylmethyl cellulose, hydroxypropyl cellulose and carboxymethyl cellulose and their salts, and the like or combinations thereof. Suitable diluents include, but are not limited to, starch, microcrystalline cellulose, lactose, dextrose, sucrose, xylitol, mannitol, maltose, polyols, magnesium hydroxide, dicalcium phosphate, coprocessed mannitol, calcium silicate and the like or combinations thereof. Suitable carriers for liquid preparations may include, but are not limited to, sorbitol, high fructose corn syrup, water, saline solution, syrup, dichloromethane, glycerine, propylene glycol, acetone, ethyl acetate, ether, dioxane, tetrahydrofuran and the like or any combinations thereof. Suitable solvents as discussed herein above may be used as solvents or cosolvents in the particulate delivery systems of the present invention. Suitable salivating agents include, but are not limited to, micronised polyethylene glycol, sodium chloride or precipitated micronised silica, and the like or combinations thereof. Suitable surfactants as those described hereinabove under preparation of carrier particles may be employed. In an embodiment, the surfactants employed in the delivery vehicle may act as suspending agent, emulsifying agent, stabilizers, or solubilizer depending on the active agent, carrier particles and final dosage form. Suitable tonicity adjusting agents include, but are not limited to, gelatin, mannitol, lactose, dextrose, sodium chloride, sodium sulfate, sorbitol and the like or combinations thereof. Suitable cryoprotectants include, but are not limited to sucrose, maltose, mannitol, lactose, trehalose, dextrans, and polyvinyl pyrollidone and the like or combinations thereof. Suitable penetration enhancers as discussed hereinabove may be employed. Suitable waxes and oils that may be included are those described hereinabove depending on the active, carrier particles and final dosage form. Suitable propellants include, but are not limited to hydrocarbons, hydrocarbon ethers and the like or combinations thereof. Suitable preservatives that may be employed include, but are not limited to, methylparaben, propylparaben, sodium benzoate, benzalkonium chloride, phenol, benzyl alcohol, chlorobutanol and the like or combinations thereof. Suitable sweetening agents that may be employed include, but are not limited to, aspartame, stevia extract, glycyrrhiza, saccharine, saccharine sodium, acesulfame, sucralose, dipotassium glycyrrhizinate, galactose, fructose, high fructose corn syrup, dextrose, sucrose, sugar, maltose, partially hydrolyzed starch, corn syrup solids, sorbitol, xylitol, mannitol and the like or mixtures thereof. Suitable natural and/or artificial flavors such as, but not limited to, mint flavour, orange flavour, lemon flavors, strawberry aroma, vanilla flavour, raspberry aroma, cherry flavor, tutty frutty flavor, magnasweet 135, key lime flavor, grape flavor, trusil art 511815, and fruit extracts and the like or combinations thereof may be employed, if required. Suitable colorants include, but are not limited to, pigments and dyes such as FD&C Red, FD&C Yellow, FD&C Green, and FD&C Blue and the like or combinations thereof. Suitable viscosity modifying agents include, but are not limited to, coprocessed microcrystalline cellulose such as but not limited to, Avicel RC591, Avicel CL-611, D-sorbitol solution, polyalkylene oxides such as, but not limited to polyethylene oxide; cellulose ethers such as, but not limited to hydroxyethyl cellulose, hydroxypropylcellulose, hydroxypropyl methyl cellulose, methyl cellulose, ethyl cellulose, sodium carboxy methylcellulose, calcium carboxymethyl cellulose, microcrystalline cellulose; gums such as but not limited to gum arabic alginates, agar, sodium alginate guar gum, locust bean, carrageenan, tarn, gum arabic, tragacanth, pectin, xanthan, gellan, maltodextrin, galactomannan, pullulan, laminarin, scleroglucan, gum arabic, inulin, karaya, whelan; polyols such as, but not limited to dipropylene glycol, polypropylene glycol, propylene glycol, polyethylene glycol (PEG), sorbitol and glycerol; carbopol, carbopol 940, starch and starch-based polymers such as, but not limited to, pregelatinized starch, acrylic acid and methacrylic acid polymers, and esters thereof, maleic anhydride polymers; polymaleic acid; poly (acrylamides); poly(olefinic alcohol)s; poly(N-vinyl lactams); polyoxyethylated saccharides; polyoxazolines; polyvinylamines; polyvinylacetates; polyimines; povidone, vinylpyrrolidone/vinyl acetate copolymer and polyvinyl acetate, mixture of polyvinyl acetate and polyvinylpyrrolidone, chitin, cyclodextrin, gelatin, chitosan and the like or any mixtures thereof. In one embodiment, viscosity modifiers may be employed as thickening agents or gelling agents depending upon the dosage form. Suitable neutralizing agents that may be employed include, but are not limited to, sodium and potassium hydroxide, diethanolamine (DEA) and aminomethyl propanol, and the like or combinations thereof. Suitable souring agents include, but are not limited to, monosodium fumarate and/or citric acid and the like or combinations thereof. Suitable humectants that may be employed include, but are not limited to, glycerin, polypropylene glycol, polyethylene glycol, lactic acid, pyrrolidone carboxylic acid, urea and the like or combinations thereof. Suitable emollients include, but are not limited to, mineral oils, lanolin, petrolatum, capric/caprylic triglyceraldehydes, cholesterol, silicones, almond oil, jojoba oil and the like or combinations thereof. Suitable antioxidants that may be employed include, but are not limited to, ascorbic acid and its derivatives, tocopherol and its derivatives, butyl hydroxy anisole and butyl hydroxy toluene and the like or combinations thereof. Suitable pH modifiers, as listed hereinabove may be employed. Suitable plasticizers that may be employed include, but are not limited to, dibutyl sebacate, propylene glycol, polyethylene glycol, polyvinyl alcohol, triethyl citrate, acetyl triethyl citrate, acetyl tributyl citrate, tributyl citrate, triacetin, sugar alcohols, glycerol or the like or any combinations thereof. In one of the embodiment, the solid dosage form of the present invention may be optionally coated. The coating may be carried out using any conventional technique employing conventional ingredients suitable for oral use. A surface coating can, for example, be in the form of a film using conventional polymers including, but not limited to, hydroxypropyl methyl cellulose, hydroxypropyl cellulose, carboxymethyl cellulose, polyvinyl alcohol polymethacrylates and the like, and combinations thereof.

In one embodiment, one or more pharmaceutical excipients discussed above may be employed in the preparation of the delivery vehicle for the carrier particles in the particulate delivery system of the present invention as required. In a further embodiment, suitable method for the preparation of carrier particles as discussed above may be utilized depending on the type of drug to be delivered, the type of carrier particle to be prepared, the carrier particle size desired, the route of administration, the final dosage form and the therapeutic effect and release profile required. In a further embodiment, the particulate delivery systems of the present invention may be for immediate release of one or more active agents at the site of action. In another embodiment, the particulate delivery systems of the present invention may be for immediate release of one or more active agents. In one embodiment, the particulate delivery systems of the present invention may be for modified release of one or more active agents. In a further embodiment, the particulate delivery systems of the present invention may be for sustained release of one or more active agents. In one embodiment, the particulate delivery systems of the present invention may be for delayed release of one or more active agents. In another embodiment, the release profile of at least one active agent from the particulate delivery system of the present invention is sigmoidal. In a further embodiment, the release profile of at least one active agent from the particulate delivery system of the present invention is pulsed. In a further embodiment, release of one or more active agents from the particulate delivery system of the present invention is immediate, sustained, delayed or any combinations thereof. In one embodiment, the particulate delivery systems of the present invention are for targeting specific biological tissues. In another embodiment the particulate delivery system of the present invention is for colon specific delivery. In a further embodiment the particulate delivery system of the present invention is for targeting the cancerous cells. In a further embodiment, the particulate delivery system of the present invention is for treatment of colorectal cancer. In another embodiment, the particulate delivery system of the present invention is for treatment of colon cancer. In one embodiment, the particulate delivery system of the present invention is for treatment of breast cancer. In another embodiment, the particulate delivery system of the present invention is for immunization. In another embodiment, the particulate delivery system of the present invention is for targeted immunization. In a further embodiment, the particulate delivery system of the present invention is for treatment of acne or psoriasis. In a further embodiment, the particulate delivery system of the present invention is for the delivery of at least one anti-cancer agent. In another embodiment, the particulate delivery system of the present invention is for delivery of at least one anti-acne agent. In a further embodiment, the particulate delivery system of the present invention is for delivery of at least one anti-psoriartic agent. In one embodiment, the particulate delivery system of the present invention is for the delivery of at least one immunological agent. In a further embodiment, the delivery system of the present invention is for targeting at least one active agent to specific biological tissue. In another embodiment, the delivery system of the present invention is for controlled delivery of at least one active agent.

In a further embodiment, the particulate delivery systems of the present invention can be prepared according to methods well known to those skilled in the art. Method of preparation of the compositions of the present invention depends on the final dosage form desired. In one embodiment, the various dosage forms as discussed hereinabove may be prepared by methods and processes known in the art. In a further embodiment, a method of preparing particulate delivery system of the present invention comprises (i) preparing plurality of particles of fenugreek gum, at least one pharmaceutically acceptable excipient and optionally at least one active agent and optionally (ii) incorporating the particles in at least one delivery vehicle.

In a further embodiment is provided use of the particulate delivery systems of the present invention for the prevention, treatment, management or mitigation of various disease conditions or disorders depending on the active agent employed. The diseases, disorders, or conditions can be selected from the group consisting of cancers, inflammatory bowel disease, acne, hyperhidrosis, unwanted sweating, bromhidrosis, body odor, chromhidrosis, excess sebum-producing disorders, seborrhea, seborrheic dermatitis, rosacea, hair loss, psoriasis, dermal infections, viral infection, bacterial infection, fungal infection, actinic keratosis, eczematous dermatitis, atopic dermatitis, burns, Raynaud's phenomenon, lupus erthythematosus, hyperpigmentation disorders, melasma, hypopigmentation disorders, vitiligo, arthritis, osteoarthritis, bruxism, cervical neck pain, dry eyes, gastrointestinal disorders, achalasia, esophageal spasm, gastroparesis, spasm of the sphincter of oddi, anal fissure, anismus, lateral epicondylitis, back pain, lower back pain, upper back pain, masseter muscle hypertrophy, facial nerve disorders, facial wrinkles, wrinkles involving the forehead, glabellar, rhytids and/or periorbital regions, unsightly facial expressions, neck lines, hyperfunctional facial lines, hyperkinetic facial lines, platysma bands, neuromuscular disorders and conditions involving muscular spasm or contracture, facial palsy such as hemi facial spasm, cerebral palsy, spasticisty due to stroke, blepharospasm, facial contracture, dystonia, cervical dystonia, laryngeal dystonia, oromandibular dystonia, writer's cramp, neuralgias, trigeminal neuralgia, neuropathic pain, Parkinson's disease, plantar fasciitis pain, prostate hyperplasia, headache, migraine, essential headache, cervicogenic headache, tension headache, prostatic disorders, prostatic pain, prostatic hypertrophy, restless leg syndrome, rhinitis, allergic rhinitis, sialorrhea, skin pruritis, strabismus, temporomandibular joint ("TMJ") syndrome, tics, Tourette's syndrome, hemifacial spasm, tremor, essential tremor, urinary bladder dysfunction, detrusor sphincter dysnergia, painful bladder, bladder spasticity, overactive bladder, vaginismus, spasticity such as that resulting from multiple sclerosis, retroorbital muscle, various ophthalmologic conditions, disorders, bacterial infection, for example caused by or correlated with infection by one or more of *Staphylococcus aureus*, *Streptococcus pyogenes*, group B and C streptococci, anaerobic bacteria (e.g., *Clostridium* species), *Corynebacterium* species (e.g., *Corynebacterium minutissimum*, *Corynebacterium tenuis*, etc.), *Dermatophilus congolensis*, bacterial infection of the dermis, include, but are not limited to, impetigo, folliculitis, furunculosis, carbunculosis, hidradenitis suppurativa (i.e., bacterial infection of sweat glands and/or hair follicles), skin abscesses, cat scratch disease, cellulitis, erysipelas, ecthyma, necrotizing fasciitis, erythrasma, pitted keratolysis, trichomycosis axillaris, staphylococcal scalded skin syndrome, acute paronychia, viral infection, for example caused by or correlated with infection by one or more of herpes simplex virus (e.g., type 1 and/or type 2), varicella-zoster virus, human papillomavirus, poxvirus, etc. viral infection of the dermis include, but are not limited to, herpes labialis, genital herpes, shingles, molluscum contagiosum, warts, fungal infection, for example caused by or correlated with infection by one or more of *Trichophyton* species (e.g., *Trichophyton rubrum*), *Microsporum* species, *Epidermophyton* species, *Candida* species (e.g., *Candida albicans*), *Pityrosporum ovale*, fungal infection of the dermis, include, but are not limited to, dermatophytosis, tinea pedis ("athlete's foot"), candidal intertrigo, thrush, paronychia, angular cheilitis, candidal vulvovaginitis, balanitis, tinea versicolor, chronic paronychia, bacterial infection of the dermis, viral infection of the dermis, and the like.

In further embodiment, the diseases, disorders, or conditions can also be selected from the group consisting cellular proliferation or hyperproliferation, such as cancers like breast cancer (such as metastatic breast cancer), pancreatic cancer (such as metastatic pancreatic cancer or locally advanced unresectable pancreatic cancer), multiple myeloma, renal cell carcinoma, melanoma (such as metastatic melanoma), colon cancer, colorectal cancer, renal, and gastric cancer, carcinoma, lymphoma, blastoma, sarcoma, and leukemia, squamous cell cancer, lung cancer (including small cell lung cancer, non-small cell lung cancer, adenocarcinoma of the lung, and squamous carcinoma of the lung, including squamous NSCLC), cancer of the peritoneum, hepatocellular cancer, gastric or stomach cancer (including gastrointestinal cancer), glioblastoma, cervical cancer, ovarian cancer, liver cancer (such as hepatocellular carcinoma), bladder cancer, hepatoma, melanoma, endometrial or uterine carcinoma, salivary gland carcinoma, kidney or renal cancer, prostate cancer (such as advanced prostate cancer), vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome, metastatic cancer (that is, cancer that has metastasized from the primary tumor), breast cancer (which may be HER2 positive or HER2 negative), including, for example, advanced breast cancer, stage IV breast cancer, locally advanced breast cancer, and metastatic breast cancer, lung cancer, including, for example, non-small cell lung cancer (NSCLC, such as advanced NSCLC), small cell lung cancer (SCLC, such as advanced SCLC), and advanced solid tumor malignancy in the lungs, head and neck cancer, gastric malignancies, and solid tumors (such as advanced solid tumors), non-Hodgkins lymphoma (NHL), carcinoid carcinoma, mesothelioma, gliomas, glioblastomas, neuroblastomas, and multiple myeloma, early stage pancreatic cancer or advanced or metastatic pancreatic cancer, melanoma, such as stage III or IV melanoma, hemorrhage, ulceration, pain, enlarged lymph nodes, cough, jaundice, swelling, weight loss, cachexia, sweating, anemia, paraneoplastic phenomena, thrombosis, etc, hyperproliferative disease, a cancer, or an inflammatory disease, prevention of restenosis, agents for treating renal disease, intermittent claudication, treatment of hypotension and shock, cardiovascular indications, to treat head trauma, assist with memory (e.g., to treat Alzheimer's/senility/dementia), migraine, movement disorders, multiple sclerosis, narcolepsy/sleep apnea, stroke, tardive dyskinesia; chronic graft versus host disease, eating disorders, learning disabilities, minimal brain dysfunction, obsessive compulsive disorder, panic, alcoholism, drug abuse, developmental disorders, diabetes, benign prostate disease, sexual dysfunction, rejection of transplanted organs, xerostomia, AIDS patients with Kaposi's syndrome; antineoplastic hormones, biological response modifiers for cancer treatment, leukemia, cancer of the lymph node or lymph system, bone cancer, cancer of the mouth and esophagus, brain cancer etc.

In a further embodiment, the present invention relates to method of treating one or more diseases or disorders listed herein above comprising administering to the subject in need thereof particulate delivery systems comprising plurality of particles comprising fenugreek gum. In one embodiment, the present invention relates to the use of particulate delivery systems of the present invention for treatment, prevention, or mitigation of one or more diseases and disorders listed hereinabove. In another embodiment, the present invention relates to particulate delivery system for administration to mammals. In a further embodiment, the present invention relates to particulate delivery system for administration to humans or animals. In one embodiment, the present invention relates to a method of treating a disease or disorder comprising administering to a subject in need thereof the delivery system of the present invention comprising plurality of particles of fenugreek gum, at least one active agent and at least one pharmaceutically acceptable excipient. In another embodiment, the present invention relates to a method of treating cancer comprising administering to a subject in need thereof the particulate delivery system of present invention comprising plurality of particles of fenugreek gum, at least one anti-cancer agent, and at least one pharmaceutically acceptable excipient. In a further embodiment, the present invention relates to a method of treating skin conditions or disorders comprising administering to a subject in need thereof the delivery system of the present invention comprising plurality of particles of fenugreek gum, at least one active agent for treating the skin condition or disorder and at least one pharmaceutically acceptable excipient. In a further embodiment, the present invention provides use of fenugreek gum for the manufacture of carrier particles of the particulate delivery system of the present invention.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed, but that the invention will include all embodiments falling within the scope thereof. Details of the present invention, including its objects and advantages, are provided in the non-limiting exemplary illustrations below.

EXAMPLES

Example 1: Fenugreek Gum Nanoparticles

A: Preparation of Fenugreek Gum Nanoparticles by Precipitation-Solvent Evaporation Method The gum solution was prepared by dissolving 1 gm of fenugreek gum in 100 ml pH7.4 phosphate buffer. 50 mg glutaraldehyde was added to gum solution under stirring. 20 ml of isopropyl alcohol was poured in the above solution continuously under high pressure homogenization to obtain nanoprecipitates. The isopropyl alcohol was evaporated off in a rotary evaporator and the solution was then centrifuged and filtered to obtain nanoparticles.

B: Preparation of Fenugreek Gum Nanoparticles by Emulsion-Crosslinking Method

The gum solution was prepared by dissolving 1 gm of fenugreek gum, 50 mg borax and 20 mg of polyoxyethylene (20) sorbitan monooleate (Tween 80) in 100 ml pH 7.4 phosphate buffer. 50 ml dichloromethane was added to the gum solution under continuous stirring. Nanoprecipitates of gum were obtained. The dichloromethane was evaporated off in a rotary evaporator and the solution was then centrifuged and filtered to obtain substantially non-agglomerated nanoparticles.

Example 2: Fenugreek Gum Based Clindamycin Nanoparticles

Clindamycin phosphate (250 mg), glutaraldehyde (75 mg) and fenugreek gum (1 gm) were dissolved in 100 ml of pH7.4 phosphate buffer. 5 gm polyethylene glycol 400 was dissolved in 50 ml ethanol. This organic solution was then poured in gum solution continuously under high pressure homogenization. The ethanol was evaporated off in a rotary evaporator and the solution was then centrifuged and filtered to obtain nanoparticles. These nanoparticles may be incorporated in a suitable delivery vehicle such as cream base, ointment base and liniment base to deliver clindamycin topically.

Example 3: Enteric Coated Capsules of Methotrexate Nanoparticles

Methotrexate sodium (500 mg), fenugreek gum (0.4 gm) and hydroxypropyl methyl cellulose (HPMC K100LV) (0.1 gm) were dissolved in 50 ml of pH7.4 phosphate buffer. This mixture was allowed to swell for 1 hour. 0.1% solution of poly(oxyethylene)-poly(oxypropylene) block copolymer (poloxamer 407) was prepared in 75 ml dichloromethane. Methotrexate-gum aqueous solution was dispersed in organic phase by mechanically stirring at 2000 rpm, resulting in primary emulsion w/o in ratio of 1:1.5. Second gum solution was prepared by dissolving fenugreek gum (1 gm), 30 mg polyoxyethylene (20) sorbitan monooleate (tween 80) and 50 mg borax in water and the solution was made up to 100 ml volume. Primary emulsion of methotrexate and gum was mixed with second gum solution by mechanically stirring at 1000 r.p.m resulting in wioiw double emulsion in ratio 1:1.5:2. After evaporation of dichloromethane under reduced pressure, the nanoparticles of gum with methotrexate were subjected to centrifugation at 20,000 rpm and collected. Nanoparticles equivalent to 10 mg methotrexate base were lubricated and filled into gelatin capsules that were coated with pH dependent enteric polymer.

Example 4: Capsules of Tamoxifen Citrate Nanoparticles

Drug solution was prepared by dissolving tamoxifen citrate (20 mg) in 25 ml dichloromethane. Gum solution was prepared by dissolving 50 mg fenugreek gum, 2.5 mg glutaraldehyde, 10 mg of sorbitan monooleate (Span 80) in 50 ml pH7.4 phosphate buffer. The drug solution was poured in the gum solution under stirring. The dichloromethane was removed by evaporation. The nanoparticles were separated, and dried. Nanoparticles equivalent to 10 mg tamoxifene citrate were lubricated and filled into hard gelatin capsules.

Example 5: Clobetasol Nanogel

TABLE 1

Fenugreek gum based nanoparticles

| Ingredients | % w/w |
| --- | --- |
| Clobetasol propionate | 0.05 |
| Fenugreek gum | 2 |
| Castor oil | 8 |
| Poloxamine (Tetronic 904) | 0.5 |
| Butylated hydroxy toluene | 0.005 |
| Carbopol 940 | 2 |
| Glycerine | 3 |
| Ethanol | 5 |
| Sodium hydroxide | q.s |
| Water | q.s |

Procedure: Clobetasol propionate, castor oil and butylated hydroxy toluene were mixed in ethanol. Fenugreek gum and poloxamine (Tetronic 904) were dissolved in water. Both the solutions were mixed with vigorous stirring. The blend was homogenized to reduce the droplet size and obtain a nanoemulsion. Sodium hydroxide solution was added to aqueous dispersion of Carbopol 940 to obtain the desired pH. This aqueous dispersion was then mixed with nanoemulsion to get nanogel. This nanogel was non-irritant to skin.

We claim:

1. A particulate delivery system comprising plurality of particles comprising fenugreek gum and at least one pharmaceutically acceptable excipient, wherein the fenugreek gum comprises not less than about 15% by weight of galactomannan.

2. The delivery system of claim 1, wherein the particles are of a size of about 0.1 nm to about 1000 µm.

3. The delivery system of claim 1, wherein the particles are in the form of nanoparticles, nanospheres, nanocapsules, microparticles, microspheres, microcapsules, liposomes, nanoemulsions, solid lipid nanoparticles, or mixtures thereof.

4. The delivery system of claim 3, wherein the particles are in the form of nanoparticles, nanospheres, microparticles, microspheres, or mixtures thereof.

5. The delivery system of claim 1, wherein the fenugreek gum comprises not less than about 15% by weight of galactomannan, not more than about 80% by weight of insoluble fibers and not more than about 5% by weight of proteins.

6. The delivery system of claim 1, wherein the pharmaceutically acceptable excipient is a surfactant, a synthetic polymer, a natural polymer, a surface modifier, a crosslinking agent, solvent, a complexing agent, a lipid, a pH modifier or a mixture thereof.

7. The delivery system of claim 6, wherein the synthetic polymer is selected from a cellulose derivative, a vinyl derivative or polymer or copolymer thereof, a polyalkylene oxide and derivative thereof, a maleic copolymer, an acrylic acid derivative, a polyester, a poly (acrylamide), a polyanhydride, a pegylated polymer, copolymer and derivative thereof, a polyalkyl (cyanoacrylate) polymer, copolymer and derivative thereof, a polystyrene polymer, copolymer, and derivative thereof, a polyamine, copolymer or derivative thereof, a polyphosphazene, a polyoxazoline, or any combination thereof and the natural polymer is selected from gelatin, casein, cholesterol, tragacanth, dextran, collagen, alginate, cellulose, albumin, lectin, legumin, vicillin, pullulan, gliadin, agarose, starch, starch-based polymer, chitosan, maltodextrin, xanthan gum, guar gum, locust bean gum, gellan, konjac, inulin, karaya gum, gum acacia, heparin, hyaluronan, pectin, amino acid, spermidine, spermine, putrescine, or any mixture thereof.

8. The delivery system of claim 6, wherein the crosslinking agent is selected from glutaraldehyde, formaldehyde, glyoxal, epichlorohydrin, divinyl sulphone, divinyl benzene, genipin, N-hydroxy succinimide, carbodiimide, 1,5-dihalidopentane, 1,9-nonanedithiol, epichlorhydrin, citric acid, succinic acid, malic acid, tartaric acid ethylene glycol dimethacrylate, pentaerythritol tetracrylate, pentaerythritol triacrylate, 1-[3-(dimethyl amino) propyl]-3-ethylcarbodiimide methiodide, glycerol(bis)acrylate, 3-(acryloyloxy)-2-hydroxypropyl methacrylate, ethylene glycol diacrylate, glycerol, dimethacrylate, divinyl citrate, polycaprolactone (PCL) diacrylate, methyl methacrylate (MMA), divalent or multivalent metal ions, periodate oxidised carbohydrate containing 1,5-dialdehyde moiety, small molecule polycation or polyanion or any combination thereof.

9. The delivery system of claim 1, wherein the system further comprises at least one active agent; said active agent being a therapeutic, an immunologic or a diagnostic agent.

10. The delivery system of claim 1, wherein the system further comprises a delivery vehicle comprising at least one pharmaceutically acceptable excipient; said excipient being a disintegrant, a superdisintegrant, a lubricant, a glidant, a binder, a diluent, a salivating agent, a surfactant, a tonicity adjusting agent, a cryoprotectant, a penetration enhancer, a wax, an oil, a propellant, a preservative, a flavor, a sweetener, a colorant, a viscosity modifying agent, a plasticizer, a neutralizing agent, a souring agent, a thickening agent, a humectant, an emollient, an antioxidant, a pH modifier, a gelling agent, a solvent, or any combination thereof.

11. The delivery system of claim 1, wherein the delivery system is in the form of tablets, granules, capsules, pills, pellets, suspensions, emulsions, linctuses, mouthwashes, gargles, nanoemulsion, nanosuspensions, nanogel, caplets, enteric coated tablets, enteric coated capsules, effervescent tablet, orally disintegrating tablets, dispersible tablets, dry suspension for reconstitution, wafers, bite-dispersion tablets, gastroretentive nanospheres, poultice, pastes, dusting powders, liniments, creams, lotions, gels, ointments, drops, shampoo, conditioner, sunscreen, deodorant, antiperspirant, suppositories, enemas, aerosol, powder, face wash, body wash, eye drops, ocular creams, ocular ointments, dry powder for inhalation, solutions, or nasal sprays.

12. The delivery system of claim 1, wherein the particles are prepared by nanoprecipitation, emulsion solvent evaporation, emulsion-crosslinking, emulsion solvent diffusion, microemulsion, gas antisolvent precipitation, ionic gelation, milling or size reduction method, PEGylation, salting-out, dialysis, single or double emulsification, nanospray drying, layer by layer method, desolvation, supercritical fluid technology, or any combinations thereof.

13. The delivery system of claim 1, wherein the delivery system is for targeting at least one active agent to specific biological tissue or for controlled delivery of at least one active agent.

14. A method of treating a disease or disorder comprising administering to a subject in need thereof the delivery system of claim 9.

15. A method of treating cancer comprising administering to a subject in need thereof a particulate delivery system comprising a plurality of particles comprising fenugreek gum and at least one pharmaceutically acceptable excipient, wherein the delivery system further comprises at least one anti-cancer agent.

16. A method of treating a skin condition or disorder comprising administering to a subject in need thereof a particulate delivery system comprising a plurality of particles comprising fenugreek gum and at least one pharmaceutically acceptable excipient, wherein the delivery system further comprises at least one active agent for treating the skin condition or disorder.

17. A method of preparing particulate delivery system comprising (i) preparing a plurality of particles of fenugreek gum, wherein the fenugreek gum comprises not less than about 15% by weight of galactomannan, at least one pharmaceutically acceptable excipient and, optionally, at least one active agent, and optionally (ii) incorporating the particles in at least one delivery vehicle.

18. The method of claim 15, wherein the fenugreek gum comprises not less than about 15% by weight of galactomannan.

19. The method of claim 16, wherein the fenugreek gum comprises not less than about 15% by weight of galactomannan.

20. A method of treating cancer comprising administering to a subject in need thereof the delivery system of claim 9 wherein the active agent is an anti-cancer agent.

21. A method of treating a skin condition or disorder comprising administering to a subject in need thereof the delivery system of claim 9, wherein the active agent is an active agent for treating a skin condition or disorder.

* * * * *